(12) United States Patent
Sachdeva et al.

(10) Patent No.: US 8,113,829 B2
(45) Date of Patent: *Feb. 14, 2012

(54) UNIFIED WORKSTATION FOR VIRTUAL CRANIOFACIAL DIAGNOSIS, TREATMENT PLANNING AND THERAPEUTICS

(75) Inventors: Rohit Sachdeva, Plano, TX (US); Sanjeev Taneja, Plano, TX (US); Peer Sporbert, Berlin (DE); Phillip Getto, Plano, TX (US); Stephan Maetzel, Berlin (DE); Hans Imgrund, Berlin (DE); Charles L. Abraham, Dallas, TX (US)

(73) Assignee: Orametrix, Inc., Richardson, TX (US)

( * ) Notice: Subject to any disclaimer, the term of this patent is extended or adjusted under 35 U.S.C. 154(b) by 771 days.

This patent is subject to a terminal disclaimer.

(21) Appl. No.: 11/799,390

(22) Filed: May 1, 2007

(65) Prior Publication Data

US 2007/0207437 A1 Sep. 6, 2007

Related U.S. Application Data

(63) Continuation of application No. 10/429,123, filed on May 2, 2003, now Pat. No. 7,234,937, which is a continuation-in-part of application No. 10/340,404, filed on Jan. 9, 2003, now abandoned, which is a continuation of application No. 09/560,641, filed on Apr. 28, 2000, now Pat. No. 6,512,994, which is a continuation-in-part of application No. 09/452,034, filed on Nov. 30, 1999, now abandoned, application No. 11/799,390, which is a continuation-in-part of application No. 09/835,039, filed on Apr. 13, 2001, now Pat. No. 6,648,640.

(51) Int. Cl.
*A61C 3/00* (2006.01)

(52) U.S. Cl. ............................................ 433/24

(58) Field of Classification Search ................ 433/6, 18, 433/20, 24
See application file for complete search history.

(56) References Cited

U.S. PATENT DOCUMENTS

| | | | | |
|---|---|---|---|---|
| 4,276,570 A * | 6/1981 | Burson et al. | ................. | 382/276 |
| 4,575,805 A * | 3/1986 | Moermann et al. | ........... | 700/163 |
| 4,837,732 A * | 6/1989 | Brandestini et al. | ........... | 433/29 |
| 5,060,171 A * | 10/1991 | Steir et al. | ...................... | 345/630 |
| 5,372,502 A * | 12/1994 | Massen et al. | ................ | 433/215 |
| 6,283,858 B1 * | 9/2001 | Hayes et al. | ..................... | 463/31 |
| 6,512,994 B1 * | 1/2003 | Sachdeva | ...................... | 702/167 |
| 6,621,491 B1 * | 9/2003 | Baumrind et al. | ............ | 345/419 |
| 6,648,640 B2 * | 11/2003 | Rubbert et al. | ................ | 433/24 |
| 6,688,886 B2 * | 2/2004 | Hughes et al. | ................. | 433/24 |
| 6,767,208 B2 * | 7/2004 | Kaza | ............................... | 433/24 |
| 6,851,949 B1 * | 2/2005 | Sachdeva et al. | ............ | 433/213 |
| 7,234,937 B2 * | 6/2007 | Sachdeva et al. | ............. | 433/24 |

* cited by examiner

*Primary Examiner* — Ralph Lewis
(74) *Attorney, Agent, or Firm* — McDonnell, Boehnen, Hulbert & Berghoff LLP

(57) ABSTRACT

An integrated system is described in which digital image data of a patient, obtained from a variety of image sources, including CT scanner, X-Ray, 2D or 3D scanners and color photographs, are combined into a common coordinate system to create a virtual three-dimensional patient model. Software tools are provided for manipulating the virtual patient model to simulation changes in position or orientation of craniofacial structures (e.g., jaw or teeth) and simulate their affect on the appearance of the patient. The simulation (which may be pure simulations or may be so-called "morphing" type simulations) enables a comprehensive approach to planning treatment for the patient. In one embodiment, the treatment may encompass orthodontic treatment. Similarly, surgical treatment plans can be created. Data is extracted from the virtual patient model or simulations thereof for purposes of manufacture of customized therapeutic devices for any component of the craniofacial structures, e.g., orthodontic appliances.

31 Claims, 23 Drawing Sheets

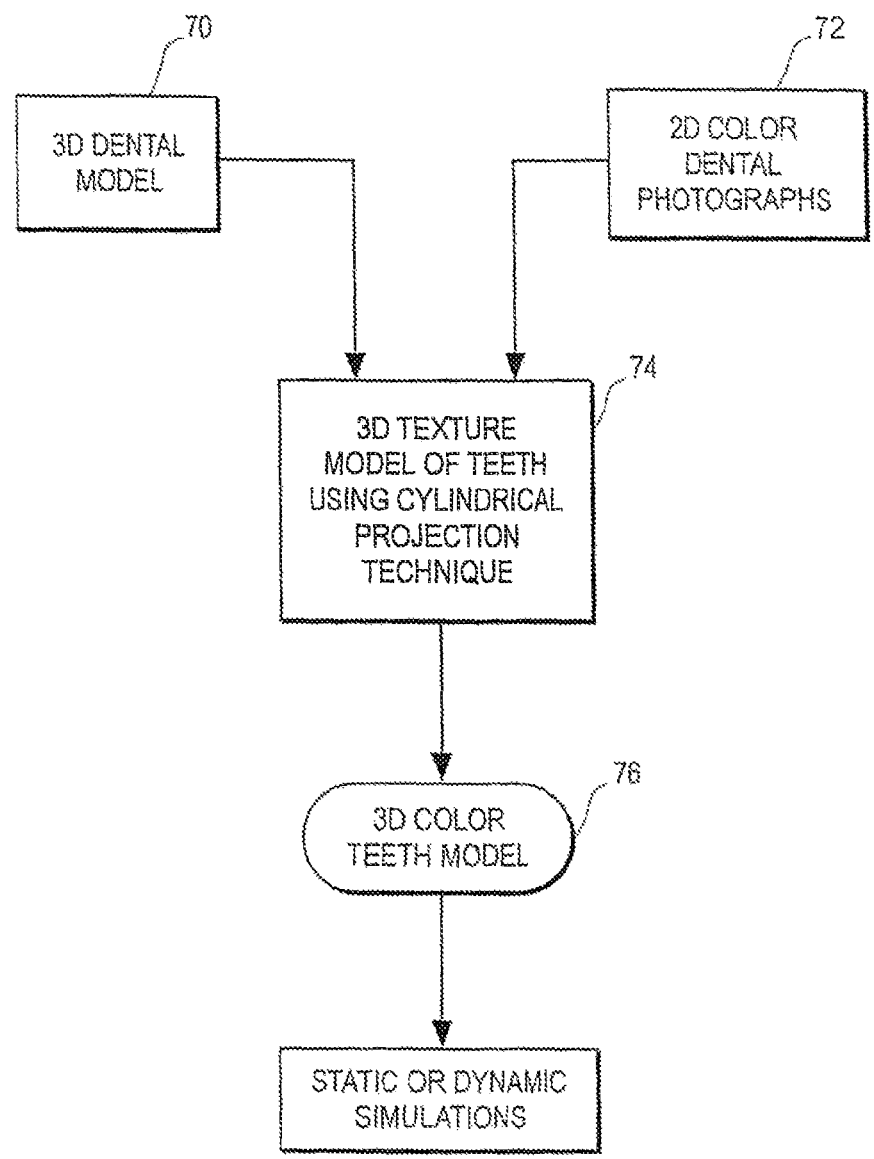

UNIFIED WORKSTATION FOR VIRTUAL CRANIOFACIAL DIAGNOSIS, TREATMENT PLANNING AND THERAPEUTICS

RELATED APPLICATIONS

This application claims priority benefits pursuant to 35 U.S.C. §120 as a continuation of application Ser. No. 10/429,123 filed May 02, 2003 now U.S Pat. No. 7,234,937, which is a continuation-in-part of application Ser. No. 10/340,404 filed Jan. 9, 2003, now abandoned, which is a continuation of application Ser. No. 09/560,641, filed Apr. 28, 2000, now U.S. Pat. No.6,512,994, which is a continuation-in-part of application Ser. No. 09/452,034 filed Nov. 30, 1999, abandoned. This application also claims priority benefits pursuant to 35 U.S.C. §120 as a continuation-in-part of application Ser. No. 09/835,039 filed Apr. 13, 2001, now U.S. Pat. No. 6,648,640. The entire contents of the related applications are fully incorporated by reference herein.

This application is also related to a patent application filed May 02, 2003, inventors Rohit Sachdeva et al., entitled INTERACTIVE UNIFIED WORKSTATION FOR BENCHMARKING AND CARE PLANNING, Ser. No. 10/429,074, pending, the entire contents of which are incorporated by reference herein.

This application is also related to a patent application filed May 02, 2003, inventors Rohit Sachdeva et al., entitled METHOD AND SYSTEM FOR INTEGRATED ORTHODONTIC TREATMENT PLANNING USING UNIFIED WORKSTATION, Ser. No. 10/428,461, pending, the entire contents of which are incorporated by reference herein.

BACKGROUND OF THE INVENTION

A. Field of the Invention

This invention relates to the field of computerized techniques for diagnosis and planning medical and dental treatment of human patients. More particularly, the invention is directed to a unified workstation and associated computerized techniques for creating a virtual three-dimensional model of the patient, including bone, soft tissue, and teeth from data from a variety of diverse imaging sources. The invention is also related to computer software tools enabling a user to use such a virtual model for diagnosis and planning treatment of craniofacial structures of the patient, including teeth, and for export of data to diverse manufacturers of therapeutic devices for the patient, such as orthodontic appliances.

B. Description of Related Art

The diagnosis and treatment of patients with craniofacial problems or disease typically begins with the obtaining of clinical history, medical history, dental history, ultrasonic scanned images, 2D or 3D scanned images, photographs, and 2D or 3D X-rays. Such X-rays are taken from the front and the side view. X-rays are also taken to show the condition of the teeth and the jaws. At this stage, diagnosis and treatment planning is often done by the practitioner on a sheet of acetate over the X-rays. Generally, this process is not very scientific, and it is time consuming and requires experience. There is no guarantee how good the results of the treatment will be. Similarly, orthodontists typically mentally visualize a target or desired occlusion for an orthodontic patient and attempt to bend archwires by hand to move teeth to the desired position. This approach also lacks reliability, reproducibility and precision.

More sophisticated, computer-based approaches to diagnosis and treatment planning of craniofacial structures, including the straightening of teeth, have been proposed. See Andreiko, U.S. Pat. No. 6,015,289; Snow, U.S. Pat. No. 6,068,482; Kopelmann et al., U.S. Pat. No. 6,099,314; Doyle, et al., U.S. Pat. No. 5,879,158; Wu et al., U.S. Pat. No. 5,338,198, and Chisti et al., U.S. Pat. Nos. 5,975,893 and 6,227,850, the contents of each of which is incorporated by reference herein. Also, imaging and medical diagnostic software and related products are marketed by Dolphin Imaging, 661 Independence Avenue, Canoga Park, Calif. 91309-2944. A method for generation of a 3D model of the dentition from an in-vivo scan of the patient, and interactive computer-based treatment planning for orthodontic patients, is described in published PCT patent application of OraMetrix, Inc., the assignee of this invention, publication no. WO 01/80761, the contents of which are incorporated by reference herein. Other background references related to capturing three dimensional models of dentition and associated craniofacial structures include S. M. Yamany and A. A. Farag, "A System for Human Jaw Modeling Using Intra-Oral Images" in *Proc. IEEE Eng. Med. Biol. Soc. (EMBS) Conf*, Vol. 20, Hong Kong, October 1998, pp. 563-566; and M. Yamany, A. A. Farag, David Tasman, A. G. Farman, "A 3-D Reconstruction System for the Human Jaw Using a Sequence of Optical Images," *IEEE Transactions on Medical Imaging*, Vol. 19, No. 5, May 2000, pp. 538-547. The contents of these references are incorporated by reference herein.

The technical literature further includes a body of literature describing the creation of 3D models of faces from photographs, and computerized facial animation and morphable modeling of faces. See, e.g., Pighin et al., *Synthesizing Realistic Facial Expression from Photographs*, Computer Graphics Proceedings SIGGRAPH '98, pp. 78-94 (1998); Pighin et al., *Realistic Facial Animation Using Image-based 3D Morphing*, Technical Report no. UW-CSE-97-01-03, University of Washington (May 9, 1997); and Blantz et al., *A Morphable Model for The Synthesis of 3D Faces*, Computer Graphics Proceedings SIGGRAPH '99 (August, 1999). The contents of these references are incorporated by reference herein.

The art has lacked a truly integrated and unified system in which soft tissue (skin, lips, etc.) and the underlying bone and other craniofacial features, including teeth, are superimposed and registered together in a common coordinate system to create a complete virtual patient model that also includes the exterior appearance of the patient, and in which the user is provided with tools to study the interaction of such craniofacial features to each other and to simulate with a computer changes in craniofacial features (such as by means of proposed tooth extraction, orthodontic manipulation, or surgery) and their effects on the external, visual appearance of the patient, and design optimal therapeutics based upon the unified virtual patient.

A principal benefit of the invention is that it provides a powerful tool to the physician, dentist or orthodontist for diagnosis and treatment planning. The unified workstation provides comprehensive, multiple functionalities in the same unit, thus eliminating the need for more expensive and less efficient multiple workstations wherein each workstation is dedicated to performing one specific function or a limited sub-set of functions necessary for the practitioner's practice. Moreover, the three-dimensional virtual patient model described herein is useful datum for use in a diverse set of possible treatment regimes for treatment of the patient. As such, the virtual patient model (or perhaps some subset of data from the model) can be provided or exported to manufacturers of appliance systems for their use in designing and/ or fabricating customized appliances for treatment of the patient, e.g., customized orthodontic appliances.

SUMMARY OF THE INVENTION

In a first aspect, a system for use in diagnosis and planning treatment of a human patient is provided. The system includes a general-purpose computer system having a processor (e.g., central processing unit) and a user interface. The details of the computer system are not important. A memory is provided which is accessible to the general-purpose computer system, such as a hard disk or a file server on a network to which the general-purpose computer is connected. The memory stores a first set of digital data representing patient craniofacial image information obtained from a first imaging device. For example, the first set of digital data may be 3-D scan data obtained from a scan of the patient's face using a scanner, 3D scan data from a scan of the dentition of the patient, X-ray data, CT scan, MRI, video, a set of two-dimensional digital color photographs of the patient, etc. The memory further includes a second set of digital data representing patient craniofacial image information obtained from a second image device different from the first image device. For example, if the first set of data represents CT scan data, the second set of data may represent 3D scan data of the teeth of the patient. The first and second sets of data represent, at least in part, common craniofacial anatomical structures of the patient. In other words, there are some anatomical features that are common to the two sets of data; they overlap to some extent. One of the first and second sets of data will typically include data representing the surface configuration or external appearance of the patient's face, for example a two dimensional digital photograph of the face (black and white or color), a 3D scan of the face, or other face data.

The system further includes a set of computer instructions stored on a machine-readable storage medium accessible to said general-purpose computer system. The computer instructions need not necessarily be stored on the same memory as the first and second sets of data. In the illustrated embodiment, the instructions are stored in the hard disk memory of the general-purpose computer system and are executed by the computer's host processor, but that need not always be the case. The set of instructions cause the general purpose computer system to perform several tasks:

1) Firstly, automatically, and/or with the aid of operator interaction, the set of instructions includes instruction that operate to superimpose the first set of digital data and the second set of digital data so as to provide a composite, combined digital representation of the craniofacial anatomical structures in a common. Preferably, but not necessarily, this representation will be a three-dimensional representation in a common 3D coordinate system. This representation is referred to herein occasionally as a "virtual patient model." In this aspect, the techniques of creation of a 3-D model disclosed in the patent application of Rohit Sachdeva et al., Ser. No. 09/560,641 filed Apr. 28, 2000 may be employed. Scaling techniques may be used to scale the data from one set of images to the other so as to created correctly scaled composite model that accurately reflects the patient's anatomy.

2) Secondly, the instructions include instructions for displaying the composite, combined digital representation of the craniofacial anatomical structures to a user of the system, for example on the user interface of the general purpose computer system.

Preferably, the instructions include instructions providing the user with tools on the user interface for visually studying the interaction of the craniofacial anatomical structures and their relationship to the external, visual appearance of the patient. The set of tools including tools for simulating changes in the anatomical position or shape of the craniofacial anatomical structures and measuring their effect on the external, visual appearance of the patient.

In a representative embodiment, 3D data of the face, skull and jaw is obtained from various scanning or imaging devices (CT scan, X-Ray, color photographs) and stored in the memory. Then, the general-purpose computer superimposes the data to place all the data in one common coordinate system to create a virtual patient model. Scaling of the data may be performed in this step. The virtual patient model is displayed to the user of the system. The software instructions in the system provide modeling or "morphing" tools which allow the user to manipulate various parameters and simulate the effect of such changes on the appearance of the patient, such as the position of one or more teeth or jaw, the shape of the arches, the age of the patient; the color and texture of the teeth; and the reflectivity and ambient conditions of the light shining on the patient.

In another aspect of this invention, an orthodontic treatment planning system is provided comprising a 3D scanner for scanning the dentition of the patient, a general-purpose computer receiving scan data from the scanner and responsively generating a three-dimensional virtual model of the dentition of the patient, and software stored on a machine-readable memory accessible to the general-purpose computer. The software contains instructions for combining, either automatically or with the aid of an operator, scan data from the scanner with digital data of the facial appearance of the patient. The digital data of the facial appearance of the patient can be obtained from a variety of sources, such as color digital camera or from a scanning of the face with the 3D scanner. The software combines (e.g., superimposes) the two sets of data to thereby create a combined digital three-dimensional representation of the dentition and the facial appearance in a common three-dimensional coordinate system.

The software further includes instructions providing the user with tools to manipulate the position of the virtual teeth in the three-dimensional virtual model of the dentition relative to other anatomical structures of the patient and to visualize the effect of proposed changes in tooth position on the facial appearance of the patient. Thus, the tools thereby provide the user with the ability to design with the computer a desired three-dimensional configuration of the virtual teeth while viewing the effect of changing tooth position on the visual appearance of the face of the patient.

In a preferred embodiment, the scanner comprises a hand-held, three-dimensional optical scanner. The digital data of the facial appearance of the patient can be obtained from the hand-held, three-dimensional optical scanner, thereby obviating the need for any other data acquisition devices. On the other hand the digital data could be obtained from a color camera, a video camera, or other type of imaging or scanning device. Other types of imaging devices could be used, such as radiographic images, CAT scan images, or MRI images.

In one possible embodiment, the system can include software combining the digital three-dimensional representation of the dentition and facial appearance with X-ray data superimposed on the scan data and the digital data of the facial appearance of the patient.

With the system of this invention, the elements of the craniofacial dental complex can be analyzed quickly in either a static or dynamic format, using the unified workstation and simulation tools provided in software in the workstation. The virtual patient model enables the simulation of facial expressions such as smiling, grimacing, the aging of the patient, and functional movements such as chewing and other complex motions of the jaw, in both a static manner and in a dynamic manner. For example, the virtual patient model is displayed and current smile of the patient is viewed, and changes to the smile are simulated, as for example by the simulation of tooth movement and its effect on soft tissue, lips etc. and its effect on the smile. The simulations could be performed as a dynamic simulation, in which the series of changes in tooth position (intermediate positions), and their effect on soft tissue during the smile, is demonstrated in a manner showing the motion of the teeth and tissues. Alternatively, the simulations could be static, for example, movement of one or more teeth from one position to another is performed, and the virtual patient model is shown with the effect on that movement on the change in soft tissue configuration (e.g., lip) or on the overall smile. There is also a possibility of simulations in between purely static simulations and dynamic simulations, such as stepping through a series of intermediate positions one at a time, essentially breaking the dynamic simulation down into a series of steps.

In the above simulations, the teeth of the patient are preferably represented as individual tooth models that are moveable relative to each other. The clinician is provided with tools to manipulate their position for diagnostic and treatment-planning purposes. Moreover, the tools provide the user the ability to simulate changes in the position or shape of the jaw, tooth or teeth, and the movement of such structures and the skull movement, and to visually observe the effect of such simulated changes on the patient's face and smile. This provides for powerful tools for study of proposed treatments for the patient. Similarly, the patient's desired feature and smile can be simulated on the user interface, and from that desired feature and smile it is possible to automatically back solve for the required jaw, and/or tooth movements or changes needed to provide that desired result, simply by comparing "before" and "after" positions of the jaw, tooth and/or skull positions.

Thus, in the broader aspects, we have invented an apparatus for assembling a virtual patient model from various data sources including 3D scanners, X-rays and 2D color camera. We have also invented a unique method for studying the interaction of craniofacial structures by varying the smile and age of the patient and the position of the teeth. For example, for the desired smile on the face, the best position of the teeth is calculated. On the other hand, the effect of various positions of the teeth on the smile can also be studied. Furthermore, we have invented a unique method for treatment planning of craniofacial structures based on the virtual patient model. By modifying various parameters, we can create multiple morphed models and multiple treatment plans quickly and reliably.

In presently preferred embodiments, the workstation also provides capabilities for integrating two and three-dimensional image data from a variety of sources, accessing treatment planning tools (software) either directly in the workstation or by furnishing data to a separate workstation that has such software, and integrating the resulting appliance design and treatment plan in a form compatible with the computer systems of diverse appliance manufacturers. In essence, the workstation facilitates a common platform by which a practitioner can integrate the acquisition of data, the treatment plan, and the appliance design and manufacture into one seamless system.

BRIEF DESCRIPTION OF THE DRAWINGS

Presently preferred embodiments of the invention are described below in reference to the appended drawings, wherein like reference numerals refer to like elements in the various views, and in which:

FIG. 4 is a flow chart showing a method of creating a complete textured three-dimensional model of teeth; simulations, either static or dynamic, can be performed with the textured 3D tooth models to simulate proposed treatments and their effect on the patient's visual appearance.

FIG. 5 also shows a plurality of icons, which, when activated, provide tools for manipulating the models shown in the Figure.

DETAILED DESCRIPTION OF PREFERRED EMBODIMENTS

General Description

A unified workstation environment and computer system for diagnosis, treatment planning and delivery of therapeutics, especially adapted for treatment of craniofacial structures, is described below. In one possible example, the system is particularly useful in diagnosis and planning treatment of an orthodontic patient. Persons skilled in the art will understand that the invention, in its broader aspects, is applicable to other craniofacial disorders or conditions.

Figure 1:
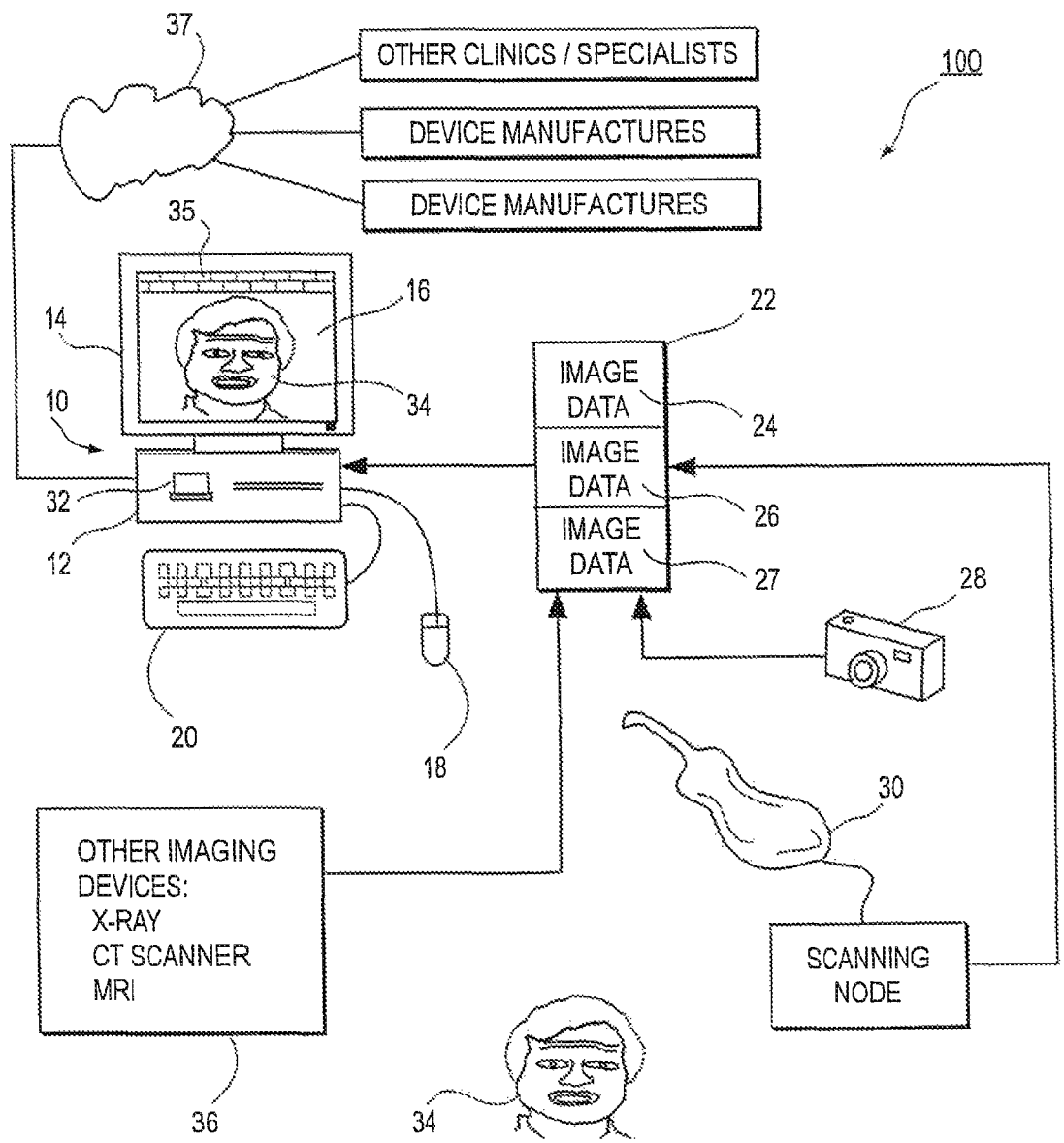
FIG. 1 is block diagram of a system for creating a three-dimensional virtual patient model and for diagnosis and planning treatment of the patient.

A presently preferred embodiment is depicted in FIG. 1. The overall system 100 includes a general-purpose computer system 10 having a processor (CPU 12) and a user interface 14, including screen display 16, mouse 18 and keyboard 20. The system is useful for planning orthodontic treatment for a patient 34. In another example, the system is particularly useful in planning therapeutics and designing customized appliances for the patient. In still another example, the system is particularly useful in integrating the required set of patient information (image data, clinical history data, etc.) to form a basis for treatment planning. The virtual patient can be used in all facets of dental care, such as planning surgical treatment, restorative dentistry, prosthodontics, design and manufacture of implants, etc.

The system 100 includes a memory 22 accessible to the general-purpose computer system 10. The memory 22 stores two or more sets of digital data representing patient craniofacial image information. These sets include at least a first set of digital data 24 representing patient craniofacial image information obtained from a first imaging device and a second set of digital data 26 representing patient craniofacial image information obtained from a second image device different from the first image device. The first and second sets of data represent, at least in part, common craniofacial anatomical structures of the patient. At least one of the first and second sets of digital data normally would include data representing the external visual appearance or surface configuration of the face of the patient.

In a representative and non-limiting example of the data sets, the first data set 24 could be a set of two dimensional color photographs of the face and head of the patient obtained via a color digital camera 28, and the second data set is three-dimensional image information of the patient's teeth, acquired via a suitable scanner 30, such as a hand-held optical 3D scanner, or other type of scanner. The memory 22 may also store other sets 27 of digital image data, including digitized X-ray photographs, MRI or ultrasound images, CT scanner etc., from other imaging devices 36. The other imaging devices need not be located at the physical location per se of the workstation system 100. Rather, the imaging of the patient 34 with one or other imaging devices 36 could be performed in a remotely located site (for example, at a clinic or hospital), in which case the image data is obtained by the workstation 100 over the Internet 37 or some other communications medium, and stored in the memory 22.

The system 100 further includes a set of computer instructions stored on a machine-readable storage medium. The instructions may be stored in the memory 22 accessible to the general-purpose computer system 10. The machine-readable medium storing the instructions may alternatively be a hard disk memory 32 for the computer system 10, external memory devices, or may be resident on a file server on a network connected to the computer system, the details of which are not important. The set of instructions, described in more detail below, comprise instructions for causing the general computer system 10 to perform several functions related to the generation and use of the virtual patient model in diagnostics, therapeutics and treatment planning.

These functions include a function of automatically, and/or with the aid of operator interaction via the user interface 14, superimposing the first set 24 of digital data and the second set 26 of digital data so as to provide a composite, combined digital three-dimensional representation of the craniofacial anatomical structures in a common three-dimensional coordinate system. This composite, combined digital three-dimensional representation is referred to herein occasionally as the "virtual patient model," shown on the display 16 of FIG. 1 as a digital model of the patient 34. Preferably, one of the sets 24, 26 of data includes photographic image data of the patient's face, teeth and head, obtained with the color digital camera 28. The other set of data could be intra-oral 3D scan data obtained from the hand-held scanner 30, CT scan data, X-Ray data, MRI, etc. The scan could be of a model of the teeth or of a facial moulage. In the example of FIG. 1, the hand-held scanner 30 acquires a series of images containing 3D information and this information is used to generate a 3D model in the scanning node 31, in accordance with the teachings of the published PCT application of OraMetrix, PCT publication no. WO 01/80761, the content of which is incorporated by reference herein. Additional data sets are possible, and may be preferred in most embodiments. For example the virtual patient model could be created by a superposition of the following data sets: intra-oral scan of the patient's teeth, gums, and associated tissues, X-Ray, CT scan, intra-oral color photographs of the teeth to add true color (texture) to the 3D teeth models, and color photographs of the face, that are combined in the computer to form a 3D morphable face model. These data sets are superimposed with each other, with appropriate scaling as necessary to place them in registry with each other and at the same scale. The resulting representation can be stored as 3D point cloud representing not only the surface on the patient but also interior structures, such as tooth roots, bone, and other structures. In one possible embodiment, the hand-held in-vivo scanning device is used which also incorporates a color CCD video camera to capture either static, dynamic or video images, which may be either black and white or in color.

The software instructions further includes a set of functions or routines that cause the user interface 16 to display the composite, combined digital three-dimensional representation of craniofacial anatomical structures to a user of the system. In a representative embodiment, computer-aided design (CAD)-type software tools are used to display the model to the user and provide the user with tools for viewing and studying the model. Preferably, the model is cable of being viewed in any orientation. Tools are provided for showing slices or sections through the model at arbitrary, user defined planes. Alternatively, the composite digital representation may be printed out on a printer or otherwise provided to the user in a visual form.

The software instructions further include instructions that, when executed, provide the user with tools on the user interface 14 for visually studying, on the user interface, the interaction of the craniofacial anatomical structures and their relationship to the external, visual appearance of the patient. For example, the tools include tools for simulating changes in the anatomical position or shape of the craniofacial anatomical structures, e.g., teeth, jaw, bone or soft tissue structure, and their effect on the external, visual appearance of the patient. The preferred aspects of the software tools include tools for manipulating various parameters such as the age of the patient; the position, orientation, color and texture of the teeth; reflectivity and ambient conditions of light and its effect on visual appearance. The elements of the craniofacial and dental complex can be analyzed quickly in either static format (i.e., no movement of the anatomical structures relative to each other) or in a dynamic format (i.e., during movement of anatomical structures relative to each other, such as chewing, occlusion, etc.). Intermediate levels of dynamic simulation are possible, as explained previously.

The workstation environment provided by this invention provides a powerful system and for purposes of diagnosis, treatment planning and delivery of therapeutics. For example, the effect of jaw and skull movement on the patient's face and smile can be studied. Similarly, the model can be manipulated to arrive at the patient's desired feature and smile. From this model, and more particularly, from the location and position of individual anatomical structures (e.g., individual tooth positions and orientation, shape of arch and position of upper and lower arches relative to each other), it is possible to automatically back solve for or derive the jaw, tooth, bone and/or soft tissue corrections that must be applied to the patient's initial, pre-treatment position to provide the desired result. This leads directly to a patient treatment plan.

These simulation tools, in a preferred embodiment, comprise user-friendly and intuitive icons 35 that are activated by a mouse or keyboard on the user interface of the computer system 10. When these icons are activated, the software instruction provide pop-up, menu, or other types screens that enable a user to navigate through particular tasks to highlight and select individual anatomical features, change their positions relative to other structures, and simulate movement of the jaws (chewing or occlusion). Examples of the types of navigational tools, icons and treatment planning tools for a computer user interface that may be useful in this process and provide a point of departure for further types of displays useful in this invention are described in the patent application of Rudger Rubbert et al., Ser. No. 09/835,039 filed Apr. 13, 2001, the contents of which are incorporated by reference herein. Additional aspects of treatment planning that are possible are set forth in the patent application of Rohit Sachdeva et al., filed on the same date as this application, entitled METHOD AND SYSTEM FOR INTEGRATED ORTHODONTIC TREATMENT PLANNING USING UNIFIED WORKSTATION, Ser. No. 10/428,461, the content of which is incorporated by reference herein.

The virtual patient model, or some portion thereof, such as data describing a three-dimensional model of the teeth in initial and target or treatment positions, is useful information for generating customized orthodontic appliances for treatment of the patient. The position of the teeth in the initial and desired positions can be used to generate a set of customized brackets, and customized archwire, which may be flat planar or otherwise in shape, and customized bracket placement jigs, as described in the above-referenced Andreiko et al. patents. Alternatively, the initial and final tooth positions can be used to derive data sets representing intermediate tooth positions, which are used to fabricate transparent aligning shells for moving teeth to the final position, as described in the above-referenced Chisti et al. patents. The data can also be used to place brackets and design a customized archwire as described in the previously cited application Ser. No. 09/835,039. Furthermore, surgical devices such as surgical archwires, splints, prosthetic devices, and restorative devices can be fabricated with these data sets. Methods of fabricated customized archwires from data sets indicating bracket position and tooth geometry are disclosed in the patent application of Werner Butscher et al., Ser. No. 09/834,967. allowed, which is incorporated by reference herein. Methods of fabricating bracket placement jigs are described in. U.S. patent application Ser. No. 09/560,127, allowed, the contents of which are incorporated by reference herein.

To facilitate sharing of the virtual patient model among specialists and device manufacturers, the system 100 includes software routines and appropriate hardware devices for transmitting the virtual patient model or some subset thereof over a computer network. The system's software instructions are preferably integrated with a patient management program having a scheduling feature for scheduling appointments for the patient. The patient management program provides a flexible scheduling of patient appointments based on progress of treatment of the craniofacial anatomical structures. The progress of treatment can be quantified. The progress of treatment can be monitored by periodically obtaining updated three-dimensional information regarding the progress of treatment of the craniofacial features of the patient, such as by obtaining updated scans of the patient and comparison of the resulting 3D model with the original 3D model of the patient prior to initiation of treatment.

Thus, it is contemplated that system described herein provides a set of tools and data acquisition and processing subsystems that together provides a flexible, open platform or portal to a variety of possible therapies and treatment modalities, depending on the preference of the patient and the practitioner. For example, a practitioner viewing the model and using the treatment planning tools may determine that a patient may benefit from a combination of customized orthodontic brackets and wires and removable aligning devices. Data from the virtual patient models is provided to diverse manufacturers for coordinated preparation of customized appliances. Moreover, the virtual patient model and powerful tools described herein provide a means by which the complete picture of the patient can be shared with other specialists (e.g., dentists, maxilla-facial or oral surgeons, cosmetic surgeons, other orthodontists) greatly enhancing the ability of diverse specialists to coordinate and apply a diverse range of treatments to achieve a desired outcome for the patient. In particular, the overlay or superposition of a variety of image information, including X-Ray, 3D teeth image data, photographic data, CT scan data, and other data, and the ability to toggle back and forth between these views and simulate changes in position or shape of craniofacial structures, and the ability to share this virtual patient model across existing computer networks to other specialists and device manufacturers, allows the entire treatment of the patient to be simulated and modeled in a computer. Furthermore, the expected results can be displayed before hand to the patient and changes made depending on the patient input.

With the above general description in mind, additional details of presently preferred components and aspects of the inventive system and the software modules providing the functions referenced above will be described next. The treatment plans developed using the virtual patient model and the unified workstation can be ones in which only one type of appliance is used to treat the patient (such as brackets and wires) or hybrid treatment plans in which multiple types or classes of appliances are used to treat the patient. Examples of hybrid treatment plans include plans in which both brackets and wires and removable aligning shells (see the Chisti et al. patents cited previously) are used during the course of treatment. The brackets and wires and removable appliances could be used at the same type for different teeth, or they could be used at different times, or both could occur.

Capture of Image Information

The creation of the virtual patient model uses the capture and storage of at least two different digital sets of image data of the patient. The image sets will typically represent, at least in part, overlapping craniofacial anatomical structures so that a superposition of them in a common three-dimensional coordinate system may occur. In a less preferred embodiment, simple two dimensional data sets could be used, in which the 2 dimensional data sets are overlapped to create a virtual patient in two dimensions. Examples of this might be using x-ray and photographs and creating the virtual patient without use of 3D data.

The type of image data that will be obtained will vary depending on the available image acquisition devices available to the practitioner, and the imaging techniques that are most pertinent for a given patient, given the totality of the circumstances. Preferably, the system employs software simulation of changes in shape or position of craniofacial structures (e.g., teeth or jaw) on the visual appearance, e.g., smile, of the patient. Accordingly, at least one of the data sets will include normally include data regarding the surface configuration of the face and head. A commercially available digital CCD camera 28 (FIG. 1), e.g., a color or black and white digital camera available from Sony or Canon, can be used to obtain this information. Preferably, the image data is color image data. The data sets are obtained by photographing the patient's head and face at various viewing angles with the camera and storing the resulting image files in the memory of the computer. These images can provide a basis for creating a morphable face model.

The image data regarding the patient's exterior appearance can be obtained through other means including via scanning of the head and face of the patient via the hand-held 3D-scanner 30 described in the published OraMetrix PCT application, publication no. WO 01/80761, incorporated by reference herein. If this approach is used, it may be beneficial to apply a thin layer of non-toxic, opaque and reflective substance to the skin prior to scanning to insure adequate data capture by the hand-held scanner. A suitable opaquing substance is described in the patent application of Nancy Butcher et al. Ser. No. 10/099,042 filed Mar. 14, 2002, entitled "Method for Wet-Field Scanning," the contents of which are incorporated by reference herein. In operation, the scanner captures a sequence of overlapping images of the surface of the patient as the scanner is held by the hand and moved about the face. The set of images can be obtained in only a few minutes. Each image is converted to a set of X, Y and Z coordinate positions comprising a cloud of points representing the surface of the face. The point clouds from each image are registered to each other to find a best fit to the data. The resulting registered point cloud is then stored in the memory as a virtual three-dimensional object. The construction, calibration and operation of the scanner, and the manner of converting scanned data to point clouds and registering three-dimensional point clouds to form a three-dimensional object is described at length in the published PCT application of OraMetrix WO 01/80761, and therefore omitted from the present discussion for the sake of brevity. Other types of scanners or coordinate measuring instruments could be used in less preferred embodiments, such as the scanning devices in the Yamany et al. articles referenced previously.

Aside from surface data of the patient obtained by the camera 28 or 3D scanner 30, the system typically will include the capture of additional data representing the teeth of the patient, and also capture of additional data representing craniofacial structures not visible to the naked eye using other imaging devices 36 (FIG. 1). For example, the system will acquire digitized images from an X-ray machine capturing X-ray photographs of the patient's head, jaw, teeth, roots of teeth, and other craniofacial structures. These photographs are digitized and stored in the memory of the computer system. Video images can be used to track functional movements such as movement of the jaws and smiling.

As other possible examples, three-dimensional magnetic resonance images of the patient's head or jaws are obtained and stored in the memory. Other examples include images acquired from a computed tomography (CT) scanner, ultrasound imager, or other type of imaging device.

While the above discussion has described how 3D image of the face can be obtained from a three-dimensional scanner, there are other possibilities that may be used in the practice of alternative embodiments. One such alternative is creating a 3D virtual face from a series of 2-D color photographs. This technique is known and described in Pighin et al., *Synthesizing Realistic Facial Expression from Photographs*, Computer Graphics Proceedings SIGGRAPH '98, pp. 78-94 (1998); Pighin et al., *Realistic Facial Animation Using Image-based 3D Morphing*, Technical Report no. UW-CSE-97-01-03, University of Washington (May 9, 1997); and Blantz et al., *A Morphable Model for The Synthesis of 3D Faces*, Computer Graphics Proceedings SIGGRAPH '99 (August, 1999), the contents of which are incorporated by reference herein. Basically, in this alternative, two-dimensional color pictures of the face are taken which are converted automatically to a textured 3 dimensional model using a 'morphable model' technique. Here, the phrase "textured 3 dimensional model" is used in the particular sense of a colorized three-dimensional object, with the word "texture" synonymous with color data, as that term is used in this particular art.

Morphable models can be built based on various known approaches such as optic flow algorithms or active model matching strategy, or a combination of both. One approach is to scan a set of 2D faces. A shape vector containing 3D vertices and texture vector containing RGB color values of each vertex represents the geometry of the face. Each face is divided into sub regions such as eyes, nose, mouth etc. Blending the sub-regions at the borders generates the complete 3D face. Automatic matching and estimating 3D face of a 2D color image from morphable model is carried out as follows:

New Shape (Sn) and texture (Tn) are computed as follows:
(1) $Sn=Sa+\Sigma\alpha s$;
(2) $Tn=Ta+\Sigma\beta t$, where Sa and Ta are the averages of Shape S and Texture T over all the 3D face datasets; s & t are the eigenvectors of the covariance matrices; $\alpha$ and $\beta$ are the coefficients of the facial shape and texture for all the faces, and n is a sub-region index.

Rendering parameters $\rho$ contain camera position, object scale, image plane rotation and translation and light intensity. From Bayes decision theory, the set of parameters, $(\alpha,\beta,\rho)$ are determined with maximum posterior probability for getting a corresponding 3D face from a 2D image.

Three-dimensional image data sets of the upper and lower arches including upper and lower teeth are preferably created with a 3D optical scanner 30, such as the OraMetrix handheld in-vivo scanner. If the 3D jaw model has no texture model, i.e., no color data, the texture data can be extracted from the 2 dimensional colored picture of the upper and lower jaw and mapped to the 3D coordinates on the jaw model using a cylindrical projection technique. In this technique, a map is constructed in texture space, that for each point (u, v), specifies a triangle whose cylindrical projection covers that point. The 3D point p corresponding to point (u, v) in texture space is computed by intersecting a ray with the surface of the corresponding point in the 2D colored image.

Superposition or Registration of the Data Sets

After the images of the face, craniofacial structures, X-rays, teeth etc. are obtained and stored in memory in digital form they are superimposed on each other (i.e., registered to each other via software in the workstation) to create a complete virtual patient model on the workstation. The superposition of the sets of image data may be developed as an automatic software process, or one in which there is user involvement to aid in the process. In one possible example, the three-dimensional textured model of the face is properly aligned with the 3D jaw model obtained from the intra-oral scan, 3D skull data from CT scan, and 2 dimensional X-rays to create a virtual patient model. For correct alignment of the data sets to each other, a preferred method executed by the software selects three or more corresponding points on the 3D jaw and the 3D face, and then computes a transformation matrix to re-orient the 3D face relative to the 3D jaw. This transformation matrix will contain the information needed to rotate and translate the 3D face relative to the 3D jaw in a best-fit manner to align the two to each other. Methods of calculation of transformation matrices to achieve registration are taught in the published PCT patent application of OraMetrix, Inc., WO 01/80761, cited previously. Similar methods are used for registering the CT scan data and X-ray data to the combined 3D face and jaw model. Once the superposition is achieved, the resulting model is displayed on the workstation user interface. The user is provided with tools for simulating movement or repositioning of craniofacial structures of the virtual patient, and the computer animates such movement or repositioning and shows the effect of such movement or repositioning on the external visual appearance of the patient.

Figure 2:
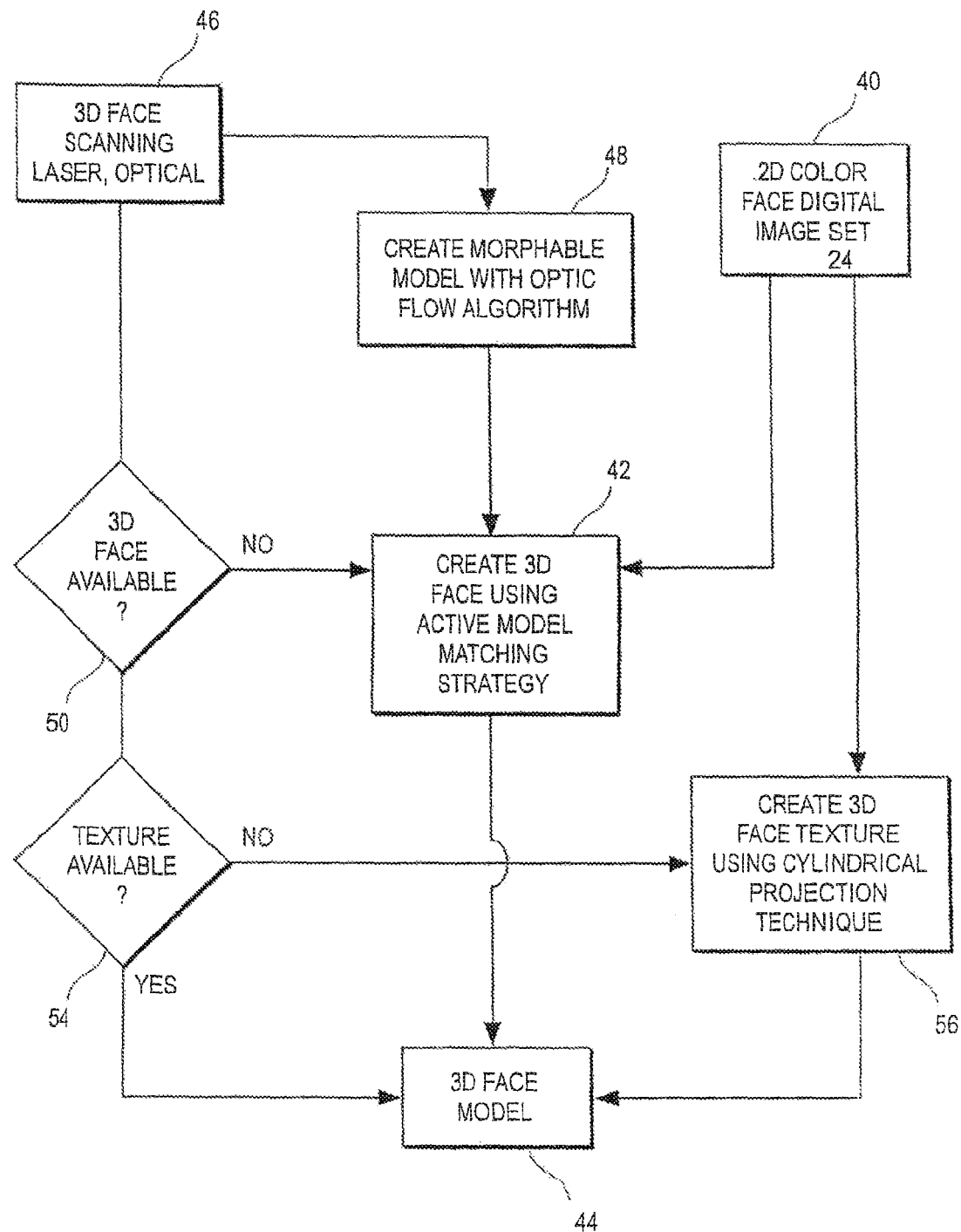
FIG. 2 is a flow chart showing a method of three-dimensional face creation from scanning systems, which may be executed in software in the computer system of FIG. 1.

An example of registering scan data of a jaw from an intra-oral scan to a 3D face model using human interaction is shown in FIGS. 2-7. FIG. 2 is a flow chart showing a software method of three-dimensional face creation from scanning systems, which may be executed in software in the computer system 10 of FIG. 1. There are two possible approaches for creating the 3D face, one using a color digital camera 28 (FIG. 1) and another using scanning of the face using the hand held scanner 30 and scanning node 31 (FIG. 1), as one possible example. Other types of scanning or imaging techniques can be used. In the situation in which a color digital camera is used, at step 40 a set 24 of 2D digital color photographic images of the face and head are obtained and stored in the memory 22 of FIG. 1. The set 24 of images is supplied to a module 42 which creates a virtual 3D face using an active model matching strategy, using the techniques known in the art and described in Pighin et al., *Synthesizing Realistic Facial Expression from Photographs*, Computer Graphics Proceedings SIGGRAPH '98, pp. 78-94 (1998); Pighin et al., *Realistic Facial Animation Using Image-based 3D Morphing*, Technical Report no. UW-CSE-97-01-03, University of Washington (May 9, 1997); and Blantz et al., *A Morphable Model for The Synthesis of 3D Faces*, Computer Graphics Proceedings SIGGRAPH '99 (August, 1999). This 3D face model is then stored in the hard disk memory of the computer 10, as indicated at process module 44.

In alternative embodiments, a 3D scanning of the face using a laser or 3D optical scanner is performed, as indicated at 44. The 3D model is provided to a module 46 which creates a morphable model of the face and head with an optic flow algorithm. This morphable model is provided to the module 42 for creating a 3D face. At step 50, the software inquires as to whether a morphable 3D face is available, and if not the processing of module 42 executes, in which a 3D morphable model of the face is created. If a morphable 3D face is already available, the software inquires at step 54 as to whether texture (color) information is available to add to the 3D face. (Note that in many 3D scanner systems there is no acquisition of color information, only spatial information). If color information is not available, the processing proceeds to module 56. In module 56, the color data is provided to the 3D model to create a 3D color morphable virtual model. The color data is supplied from the digital photographs of the patient, obtained at step 40. The texture information is supplied to the 3D model from the scanner using a cylindrical projection technique in module 56 (or by using any other known technique). The textured, morphable 3D model of the face and head is stored as indicated at module 44.

Figure 3:
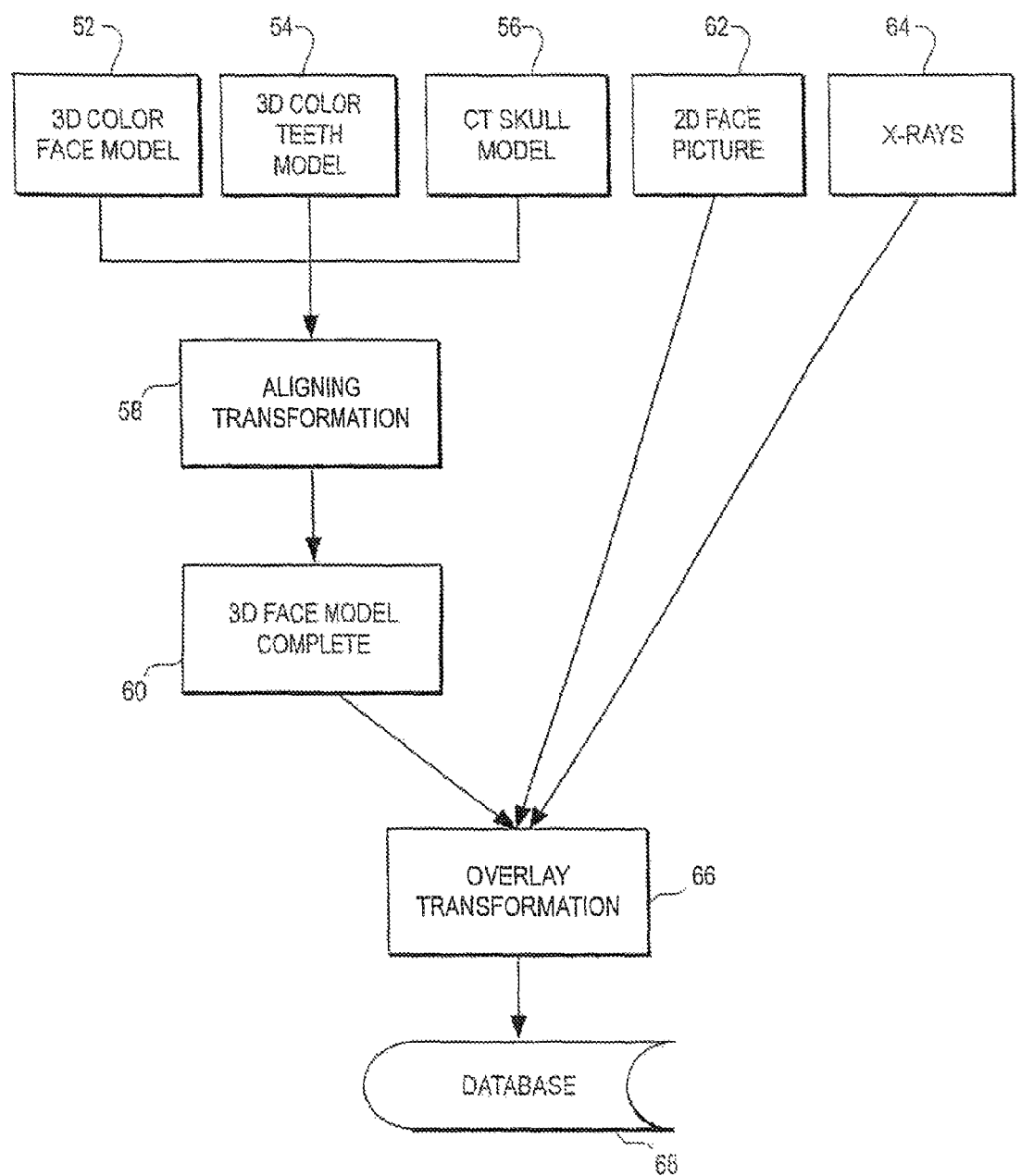
FIG. 3 is a flow chart showing an alternative method of three-dimensional face model face creation using a plurality of possible input image or data formats, which may be executed in software in the computer system of FIG. 1.

An alternative software method or process for creating a 3D model of the face is shown in FIG. 3. The method involves the acquisition of a 3D color face model 52 (using for example the techniques of FIG. 2), the acquisition of 3D color model of the teeth 54, and the acquisition of a model 56 of the skull using a CT scanner. These three models are supplied to a module 58 which performs an aligning transformation on the data sets from each of these modules. The aligning transformation process 58 basically scales and provides the necessary X, Y and Z translations and rotations to place the data sets into a common coordinate system such that common anatomical structures overlap each other. The complete 3D face model is stored as indicated at step 60 and then supplied to an overlay transformation module 66. The overlay transformation module 66 obtains a set of 2D color face photographs 62 and X-Rays 64, and overlays them to the complete 3D face model to result in a combined, composite model of the face, skull, teeth, and associated tooth roots, bone and other anatomical data. This composite representation of the patient is stored in a database 68 for the system 100.

FIG. 4 shows a process that can be used to combine 3D scan data with 2D color photographs to create a 3D color model of the teeth. In step 70, the teeth are scanned with the hand-held intra-oral scanner 30 of FIG. 1. The resulting data represent a 3D model of the dentition, which is stored in the computer 10. This process is described in the published PCT application of OraMetrix, Inc. cited previously. At step 72, 2D color photographs of the teeth are obtained with a color digital camera. In one possible embodiment, the hand-held scanner 30 includes a video camera that obtains a continuous stream of color video frames separate and apart from the acquisition of 3D image data. The color photographs of the dentition at step 72 could be obtained in this manner.

At step 74, a 3D textured model of the teeth is created using a cylindrical projection technique. Basically, in this technique, the color data from the color photographs is projected onto the tooth data. The tooth data can be represented as triangular surfaces, with the vertices of each triangle being adjacent points in a point cloud defining the surface of the tooth. The color is projected on the surfaces, and each surface is assigned a value associated with a particular color. The result is a 3D color model of the teeth. FIG. 4 further shows a step of simulating tooth movements and resulting changes on the appearance of the patient, either dynamically or statically. This step can be done regardless of whether the user chooses to create color models of teeth or whether they use non-colored models of teeth. Intermediate steps which may need to be performed, such as separation of a composite model of the entire arch into individual moveable virtual tooth objects, are not shown, but are known in the art and explained in the OraMetrix published PCT application WO 01/80761.

Figure 4A:
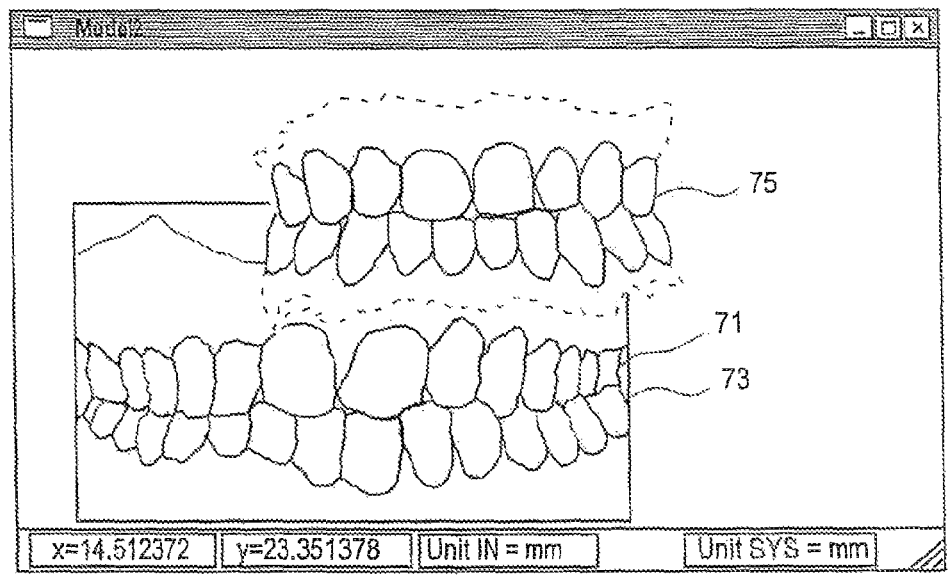
FIGS. 4A-4E show a technique for combining 2D color photographs with 3D tooth data to created textured (colored) 3D tooth models.
Figure 4B:
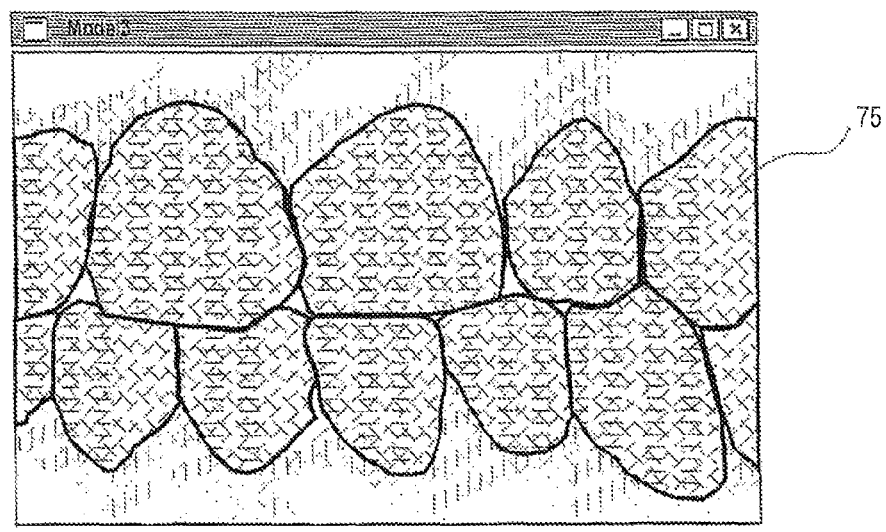

FIGS. 4A-4E show several screen displays from a user interface of the unified workstation that illustrate the process of texture mapping a 3D object (here, teeth) by projection of color data from a 2D photograph. After a patient's dentition is scanned, the virtual teeth and gingiva for both upper and lower arches are represented as a single surface, in the present example a triangle mesh surface. FIG. 4A shows a 2D digital photograph of teeth/gingivae 71 displayed in a graphical window 73 along with a 3D virtual model of the teeth 75 to one side. The 2D digital photograph 71 is scaled up or down in size as necessary to as to be approximately the same in scale (size) as the 3D model of the teeth 75. This is accomplished using any suitable icons or mouse action, such as clicking on the 2D photograph and scrolling up or down with the mouse to change the size of the 2D image so that it matches the size of the 3D model. FIG. 4B shows the surface of the teeth and gingivae of the 3D virtual model 75 in greater detail. The surface of the model 75 comprises a set of minute interconnecting triangle surfaces, with the vertices of the triangle surfaces being points that represent the surface. This is only one possible format for representing the surface of a 3D object.

Figure 4C:
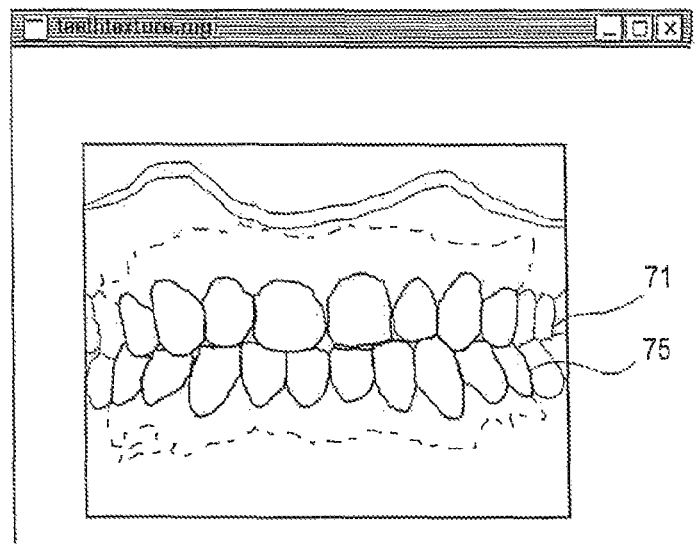
Figure 4D:
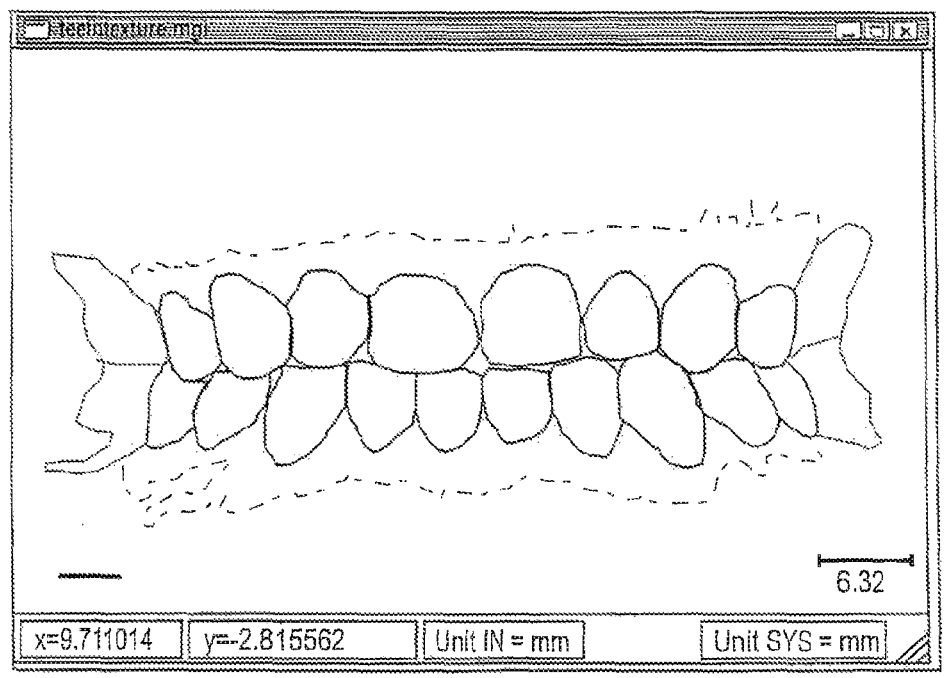
Figure 4E:
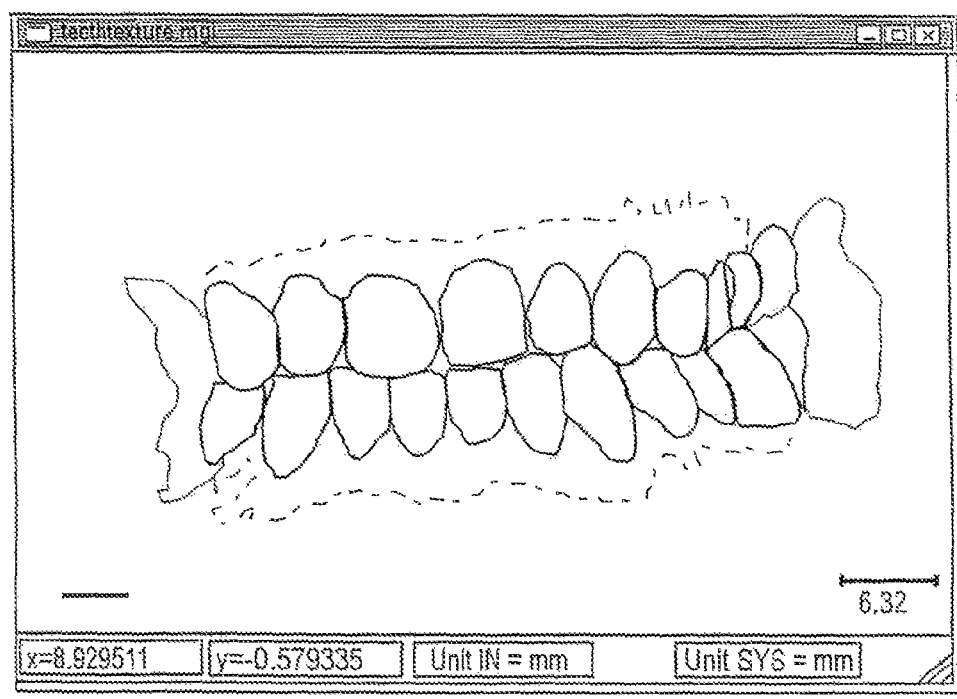

After the 2D photograph and 3D model have been scaled, a translation is performed to as to overlap the 3D model and the 2D photograph. FIG. 4C shows the 2D picture 71 transformed by scaling and translation such that it is superimposed on the 3D model 75. This superposition could be performed manually or automatically. For example, the user can click and drag the 2D digital photograph 71 and manually move it using the mouse so that it overlaps exactly the 3D model 75. The color information in the 2D photograph 71 is projected and mapped to the individual triangle surfaces forming the lower jaw and upper jaw of the 3D model 75 using, for example, a projection algorithm. The result, a textured 3D model, is shown in FIG. 4D. FIG. 4E shows a textured 3D model after rotation on the user interface.

Occlusal and lingual 2-D color photographs of each jaw are also obtained and texture data is mapped to the surface data. The result is a complete true color 3D model of the teeth of both arches.

Figure 5:
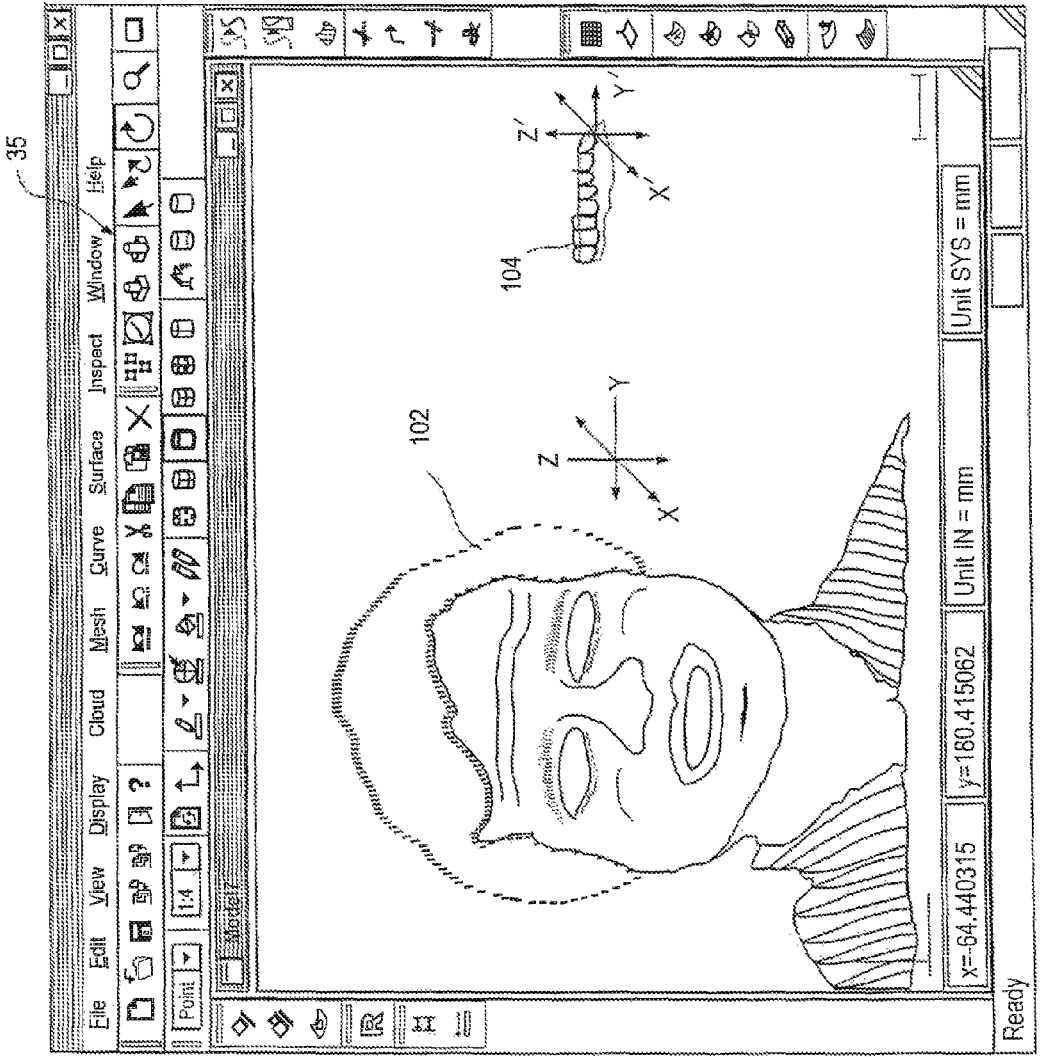
FIG. 5 is a screen shot of the user interface of FIG. 1 showing a three-dimensional face model and a three-dimensional tooth model, in separate coordinate systems (i.e., prior to registration or superposition of the two relative to each other).

FIG. 5 is an illustration of a screen display on the user interface of the computer 10. The display shows a 3D morphable model 102 of patient on the left hand side of the display, in a given arbitrary coordinate system X, Y, Z. The morphable model 102 is obtained, for example, from color photographs using the techniques described previously. A three-dimensional model 104 of teeth of the patient is shown on the right hand side of the screen. The 3D model of the teeth 104 can be obtained from intra-oral scanning using the scanner 30 of FIG. 1, from a laser scan of a physical model of the dentition obtained from an impression, from a coordinate measuring device or some other source. The source is not particularly important. The 3D model of the teeth 104 is shown in a separate coordinate system X', Y', Z'. Screen display includes various icons 35 the allow the user to position the tooth model 104 relative to the morphable model 102 in order to combine the two in a common coordinate system and construct a composite model.

Figure 6:
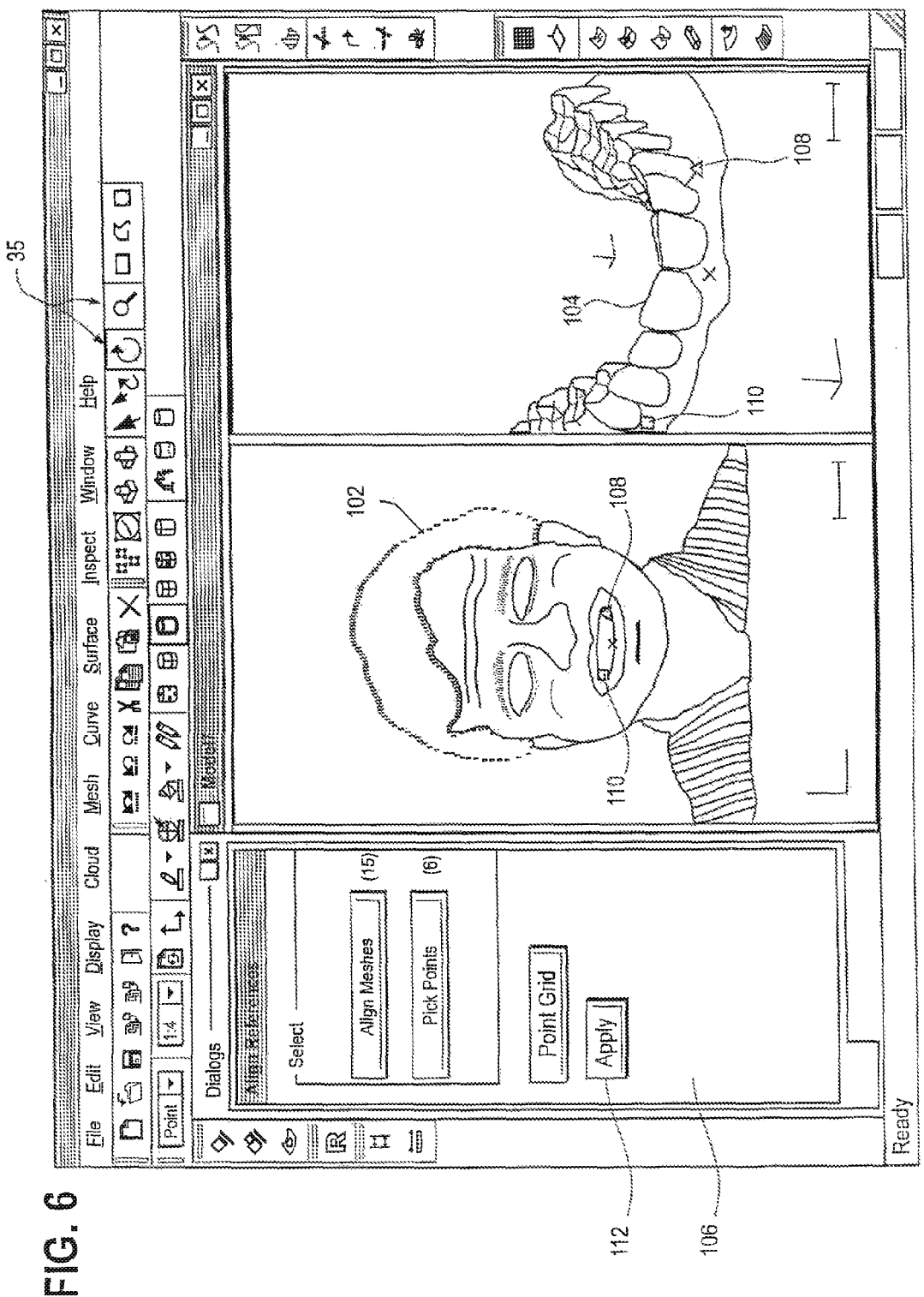
FIG. 6 is a screen shot showing one possible method of placement of the lower jaw 3D data into the face data coordinate system using corresponding points that are common to each data set.

In FIG. 6, the user has activated an "Align References" icon, which causes the screen display to show the box 106 on the left hand side of the screen. The user is provided with the option to pick points that represent anatomical structures that are common to both the morphable model 102 and the 3D tooth model 104. In this particular situation, the user has selected with the mouse two points on the lower arches which lie at the intersection of the teeth and the gums. These two points are shown as a triangle 108 and a square 110. Obviously, other points could be chosen. The user then clicks on the "Apply" tab 112. The result is shown in FIG. 7, in which the 3D tooth model 104 is combined with the morphable face 102 model to produce a combined virtual patient model 34.

Figure 7:
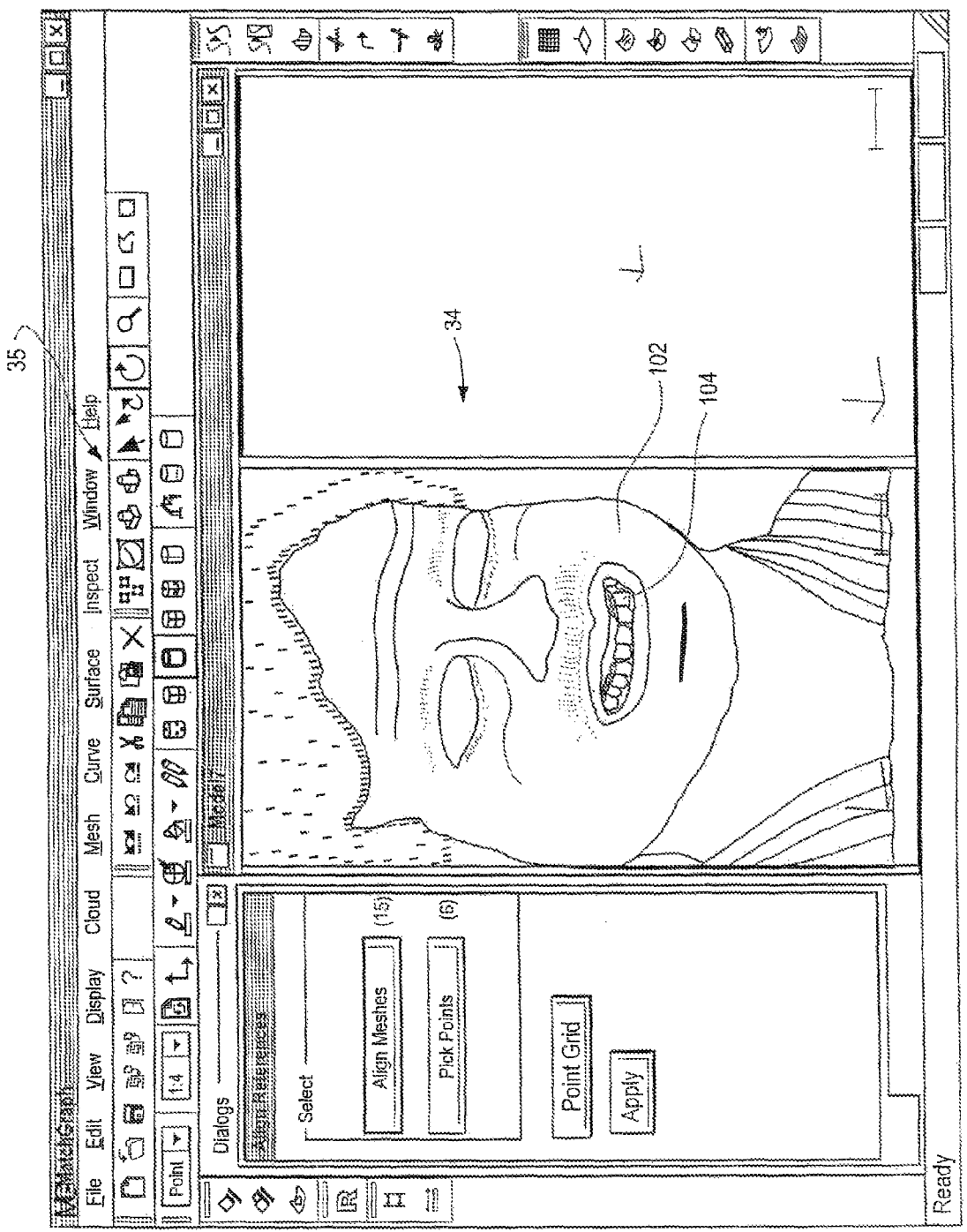
FIG. 7 is a screen shot showing the face data and the lower jaw 3D data in a common coordinate system (the face coordinate system of FIGS. 5 and 6).

In the example of FIGS. 5-7, the morphable model 102 was already scaled to the same scale as the tooth model 104. In other words, the data representing the morphable face model indicates that the spatial dimensions of the teeth in the morphable face model is substantially the same as the spatial dimensions of the virtual tooth model 104. Methods of performing scaling are described below.

Figure 8:
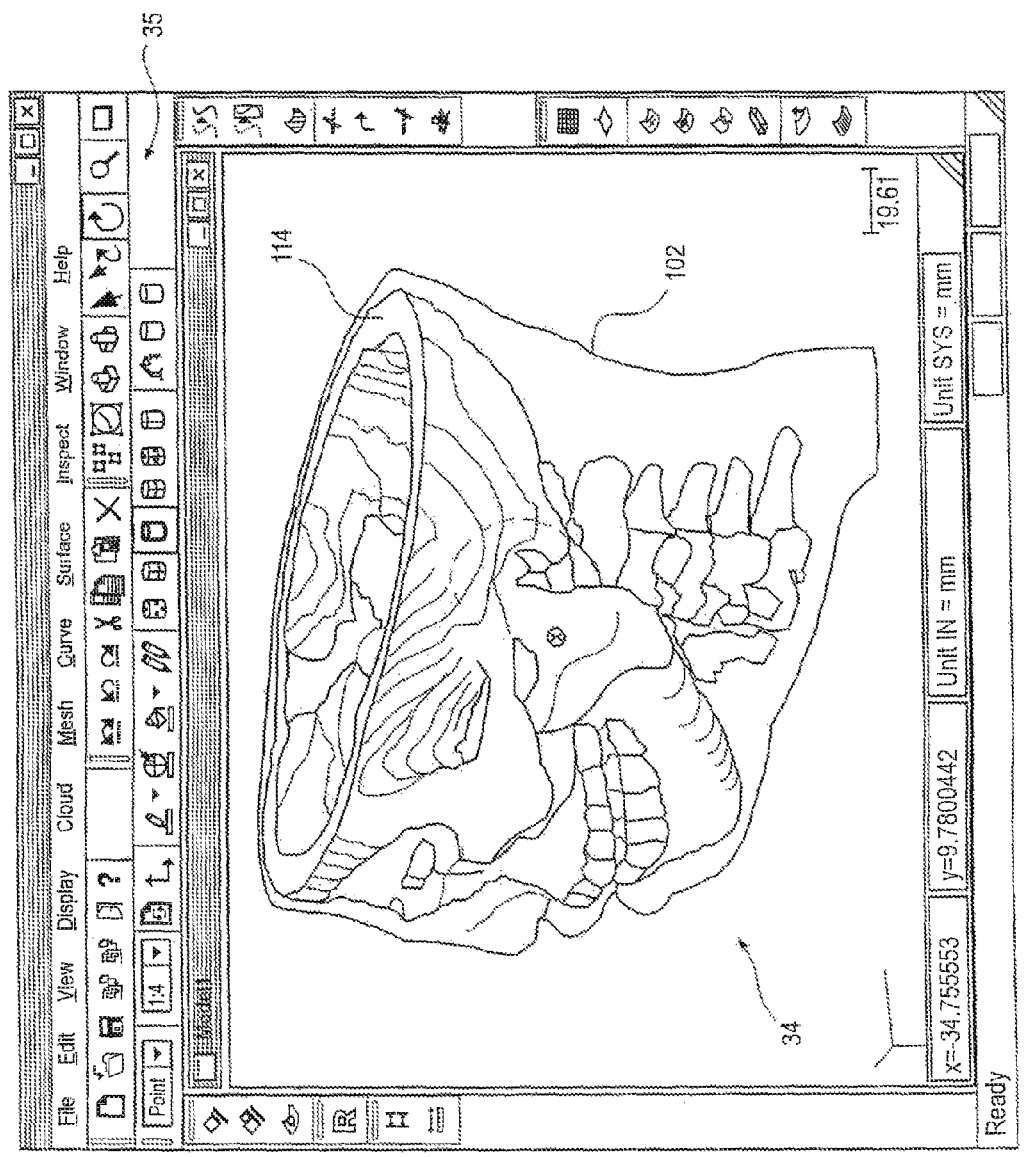
FIG. 8 is a screen shot showing the face data and skull data obtained from a CT scan in a common coordinate system.

FIG. 8 is an illustration of an alternative embodiment of a virtual patient model 34. In this embodiment, the model 34 is a combination of data 102 representing a morphable face, obtained from a plurality of 2D color photographs, and skull data 114 obtained from a CT scan. The two sets of data are shown in a common coordinate system, appropriately scaled. The manner of combining the two data sets can be using the approach described in FIGS. 6 and 7. Alternatively, the user could click and drag using a mouse one or the other of the data sets and manually position it until it is in the correct position. As yet another alternative, the software could be programmed to find common overlapping features (such as for example teeth) using surface matching algorithms, and then position the CT scan model relative to the face model such that the common features overlap exactly.

Figure 9:
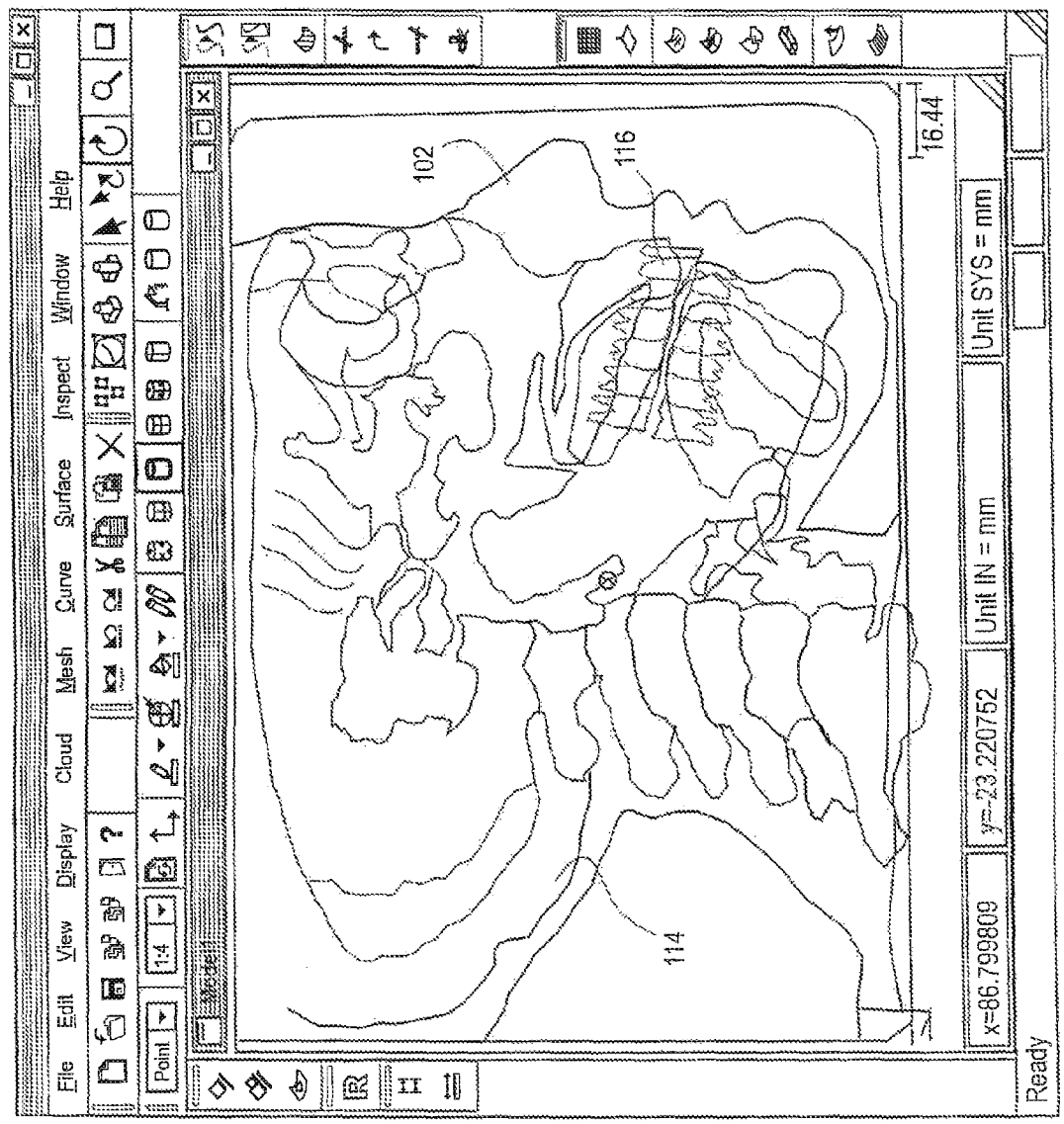
FIG. 9 is a screen shot showing face data and skull data superimposed on X-ray data obtained from the patient.

FIG. 9 is a screen shot of yet another possible embodiment of a virtual patient model. This model combines face data 102 from a morphable face model (typically obtained from 2D color photographs or a 3D scanned image of the face), skull data 114 from a 2D or 3D X-ray, and tooth data 116 obtained from a 2D or 3D image of the teeth, such as for example and in vivo scan of the patient or a scan of a model of the teeth. The manner of creating the virtual patient model can be for example using the procedure of FIG. 3 and FIG. 6-7. The morphable face model is aligned relative to the X-ray scan data either automatically or using some human interaction. The 2D X-Ray data can be morphed into 3D digital data using the morphable model algorithms cited previously. Alternatively, the 2D X-Ray data can be combined with 3D optical scan data of crowns of the teeth to create a combined X-Ray/3D tooth model, which is then combined with the X-ray/morphable face model. This process may be optimized by using virtual template tooth roots, which are modified to fit the X-ray data, and then this combined 3D root model is combined with crown data to produce a complete set of 3D teeth, including roots. This combined model is merged into the X-ray/morphable face model using the techniques of FIGS. 6 and 7 (selecting common points then using the "Apply Points" icon, FIG. 7, item 112), using click and drag techniques, or any other appropriate registration or transformation technique.

Figure 10:
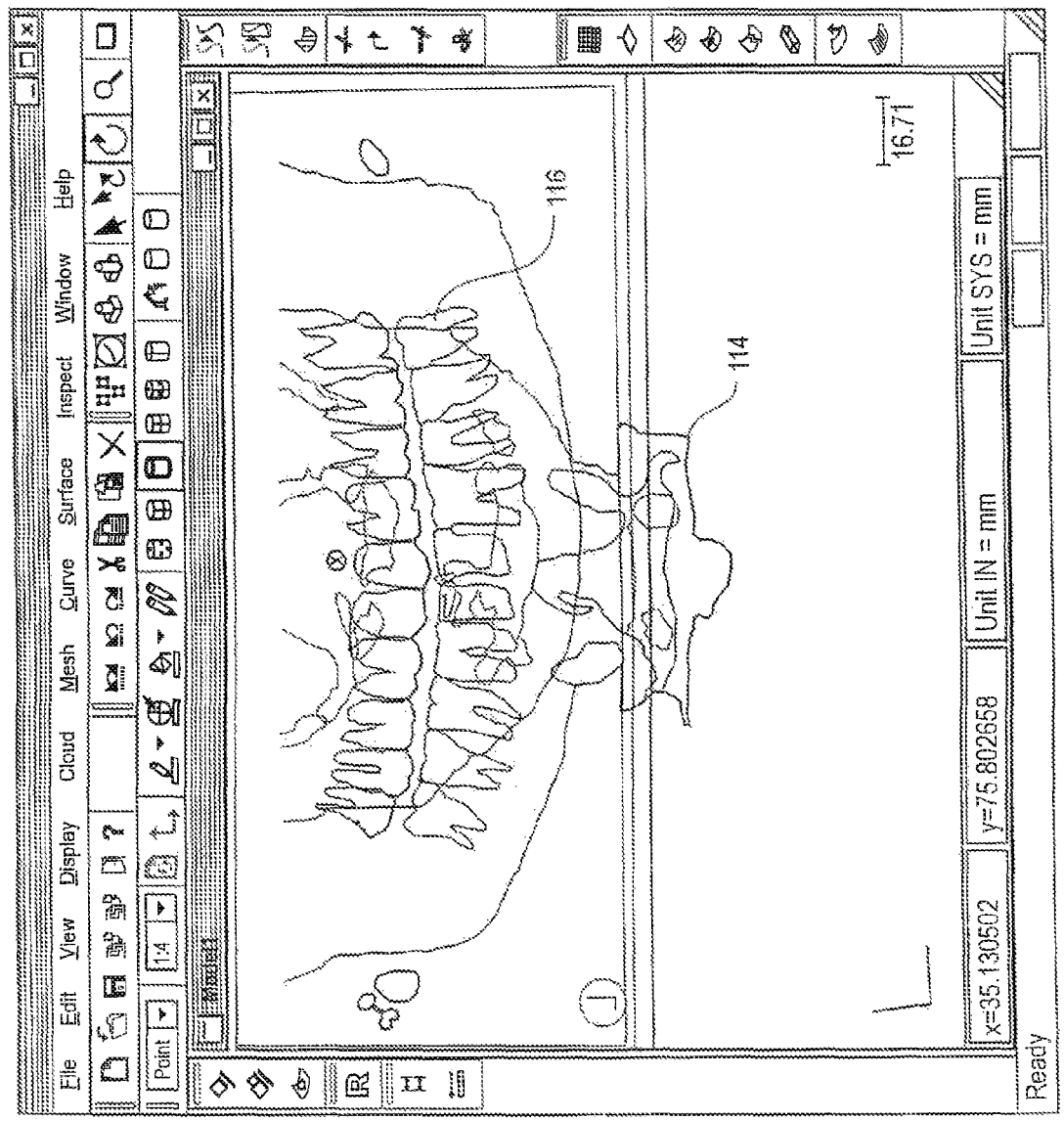
FIG. 10 is a screen shot showing the superposition of skull and face data with X-Ray data.
Figure 11A:
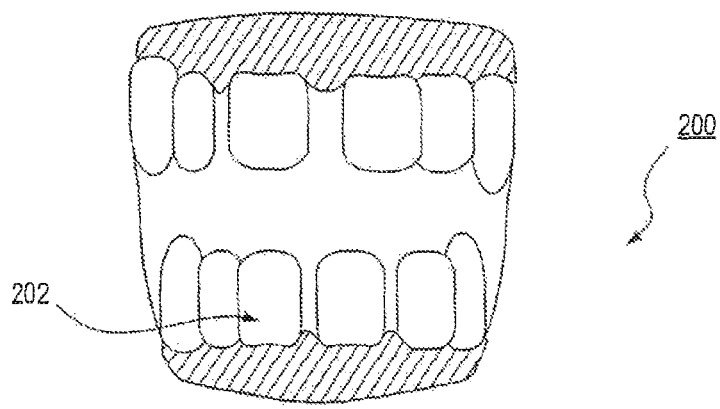
FIGS. 11A-11E are a series of views of a digital model of an orthodontic patient obtained, for example from CT scan, photographs, or intra-oral scanning with a hand-held 3D scanner.
Figure 11B:
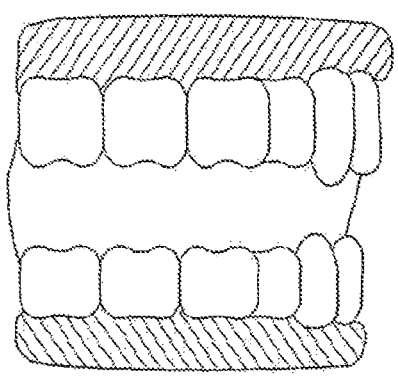
Figure 11C:
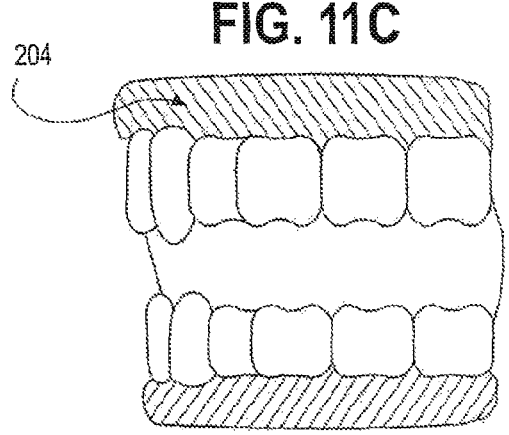
Figure 11D:
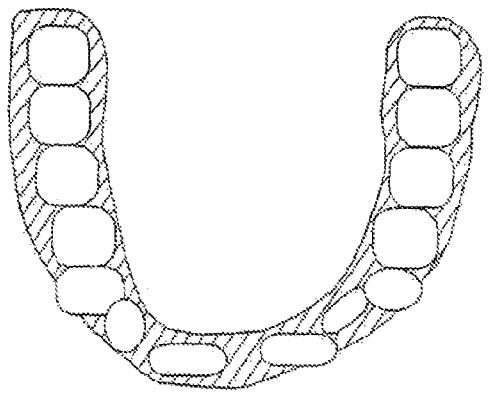
Figure 11E:
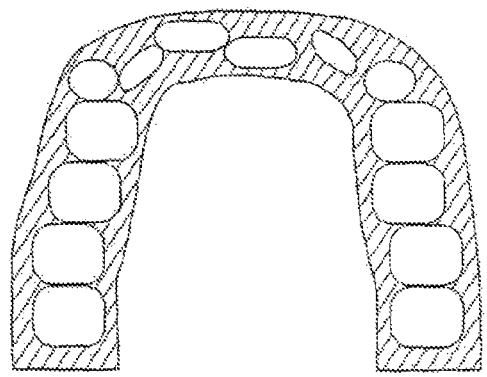

Once the virtual model is created, the user is provided with tools that allow the user to hide one or more image data in order to study certain features. Furthermore, the user is provided with navigation tools with the ability to manipulate the model so as to view it from any user-specified perspective. For example, in FIG. 10 a screen shot is shown of the superposition of skull data 114 with tooth data 116. In this example, complete 3D models of the teeth 116 are created from an in-vivo scan or scan of a model, or from some other source of scanning. Alternatively, the complete 3D tooth models 116 are created from combining X-Ray data with 3D models of teeth obtained by a scan of the crowns of the teeth (using the scanner 30 of FIG. 1 or from a laser scan of a physical model of the dentition), and/or with the use of template tooth roots that are modified to match the X-ray data.

Scaling of Data

When digital image data from multiple sources are combined or superimposed relative to each other to create a composite model, it may be necessary to scale data from one set to the other in order to create a single composite model in a single coordinate system in which the anatomical data from both sets have the same dimensions in three-dimensional space. Hence, some scaling may be required. This section describes some approaches to scaling that may be performed in one possible embodiment of the invention.

Figure 12:
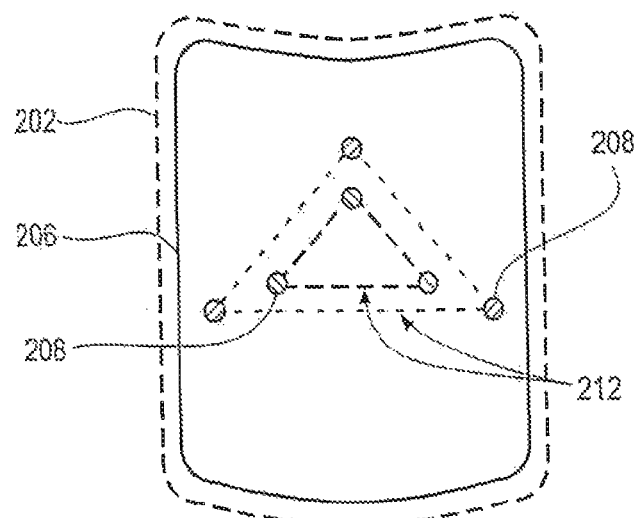
FIG. 12 is a diagram illustrating a technique for scaling orthodontic data obtained from an imaging device, such as a camera, to the actual anatomy of the patient.

FIG. 11A-11E are views of scan data 200 representing the front, right side, left side, lower and upper arches of a patient. The data includes the teeth 202 and the gingiva 204. FIG. 12 illustrates a technique of scaling the orthodontic data to match the actual orthodontic size. Depending on of the scanning technique, the orthodontic data will not completely reproduce the exact size of the teeth and other portions of the orthodontic structure. To facilitate the accuracy of the three-dimensional digital model, at least one tooth 206 can be marked utilizing one or more markings 208. The marking is done prior to obtaining the orthodontic data. Once the orthodontic data for the tooth 206 is obtained, scaling reference points 210 are also obtained. The scaling reference points are the points in the scan data that represent the image of the markings 208. A determination between the differences between the scaling reference points 210 and the actual markings 208 determine a scaling factor 212. As one of average skill in the art will readily appreciate, having the actual markings 208 and the scaling reference points 210, a variety of mathematical operations may be used to determine the scaling factor 212. For example, the coordinate differences (distance) between each of the vertices of the triangle may be utilized. As one of average skill in the art will further appreciate, a different number of markings 208 may be utilized. For example, two markings may be used or four markings may be used, etc. In addition, more than one tooth may be marked with similar markings 208. Note that the markings may be on the exterior of the patient, and a local triangulation technique may be used to obtain the scaling factor. Further note that the scaling factor 212 determination is based on an assumption that the scan data will have a linear error term in each of the x, y and z axis, such that a single scaling factor is determined and used to scale each of the teeth as well as the other aspects of the orthodontic structure of the patient.

Figure 13:
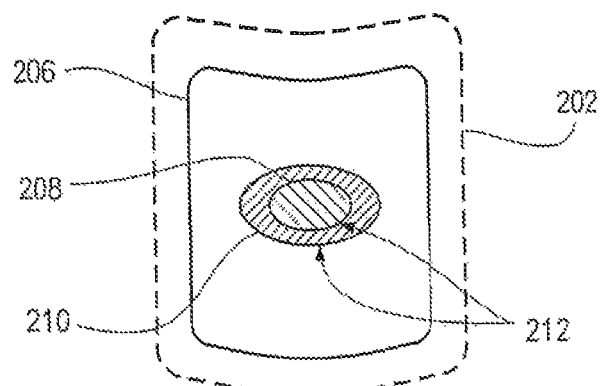
FIG. 13 is a diagram showing an alternative scaling method similar to that shown in FIG. 12.

FIG. 13 illustrates an alternate marking technique for determining a scaling factor for the orthodontic data. As shown, an actual tooth 206 is marked with a marking 208. The marking 34 is of a substantial size so as to be adequately measured. Once the orthodontic data is obtained, the orthodontic data of the tooth 202 and a corresponding scaling reference point (area) 210 are used to determine the scaling factor 212. As one of average skill in the art will readily appreciate, a simple mathematical function may be used to determine the scaling factor 212 based on the size (diameter) difference between the actual marking 34 and the scaling reference point 36. As an alternative to marking as described with reference to FIGS. 12 and 13, the actual tooth size, and the size of the model of the tooth, may be measured and used to determine the scaling factor. Accordingly, the difference between the actual tooth size the size of the tooth in the scan data will constitute the scaling factor.

When three-dimensional scanning of the type described in the published PCT application or OraMetrix is used, scaling of the three-dimensional data is not needed as a true, accurate and to scale three-dimensional image is obtained through the use of triangulation. Likewise, a true three-dimensional image can be obtained techniques such as computed tomography. However, for video or photographic data, and for X-ray data, scaling such as shown in FIGS. 12 and 13 may be needed in order to merge that data to other data such as 3D scan data.

Figure 14:
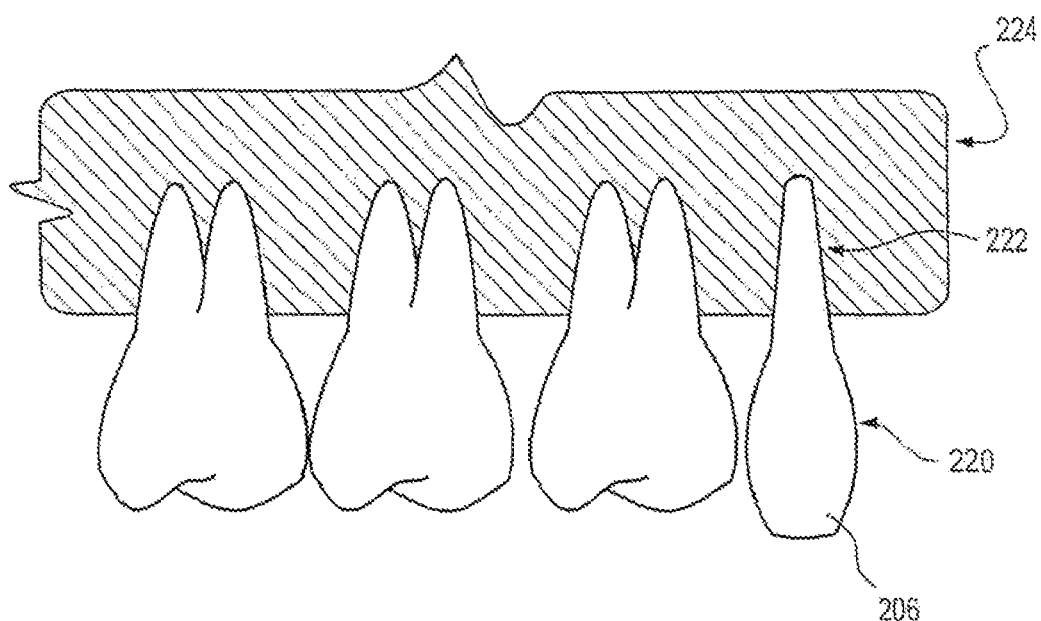
FIG. 14 is an illustration of an X-ray of a set of teeth and adjacent bone.

FIG. 14 illustrates a two-dimensional representation of image data, such as a graphical diagram of a radiographic image, such as an x-ray of a few teeth. In another embodiment, the radiographic image can be a computed tomographic image volume. As previously mentioned, the orthodontic data contains three-dimensional images of the surface of the orthodontic structure. X-rays provide a more detailed view of the teeth and surrounding hard and soft tissue as two dimensional image data. As shown in FIG. 14, each tooth 206 includes a crown 220, and a root 222 and is embedded in bone 224. Accordingly, the orthodontic data 200 of FIG. 11 only illustrates the crown 206 of the teeth. As such, a complete three-dimensional model of the orthodontic patient requires the roots and bone to be included.

Figure 15:
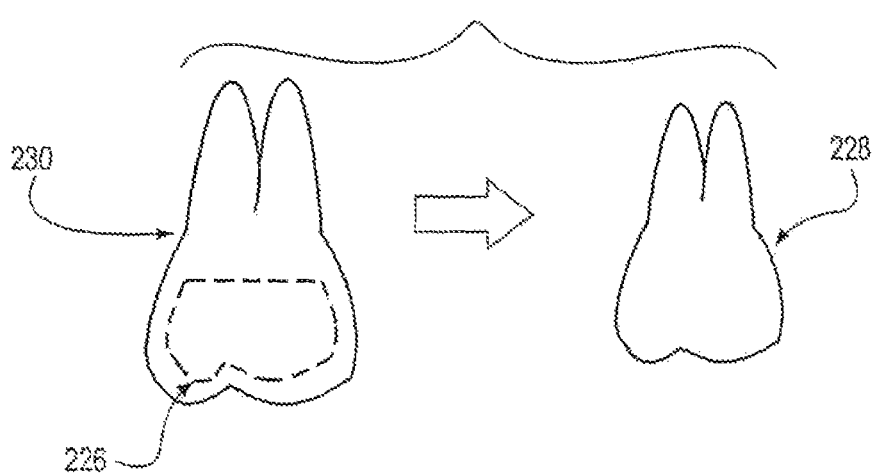
FIG. 15 is an illustration of scaling the X-ray data of the tooth to the actual size of the tooth to produce a scaled digital model of the tooth.

FIG. 15 illustrates a technique of using the scaled digital model 226 of the tooth's crown to produce an integrated or composite digital model 228 of the tooth. In this embodiment, the x-rayed data 230 of the tooth is used in comparison with the scaled digital model 226 to determine a per tooth scaling factor. The scaled digital model 226 of the tooth is positioned to be planar with the x-ray of the tooth 230. Having obtained the proper orientation between the two objects, the per tooth scaling factor is determined and subsequently used to generate the composite scaled digital model 228 of the tooth. In a specific embodiment, the per tooth scaling factor is required for current x-ray technologies, since x-rays produce a varying amount of distortion from tooth to tooth depending on the distance of the tooth from the film, the angle of x-ray transmission, etc.

To more accurately map the two-dimensional images of a tooth onto the three-dimensional model, multiple angles of the tooth should be used. Accordingly, a side, a front, and a bottom view of the tooth should be taken and mapped to the scaled digital model of the tooth. Note that the bone and other portions of the orthodontic structure are scaled in a similar manner. Further note that MRI images, and any other images obtained of the orthodontic patient, may also be scaled in a similar manner. A more complete representation of the tooth roots may be obtained using standardized, template 3D virtual tooth roots, applying the X-Ray data to the template tooth roots and modifying their shape accordingly, and them applying the modified template tooth root to the scan data of the crown to create a scaled, complete virtual tooth object including tooth roots.

Figure 16A:
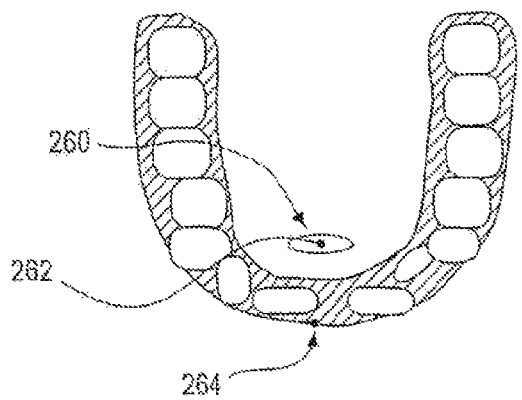
FIGS. 16A-16C is an illustration of a method of determining orientation reference points in a digital model of a patient.
Figure 16B:
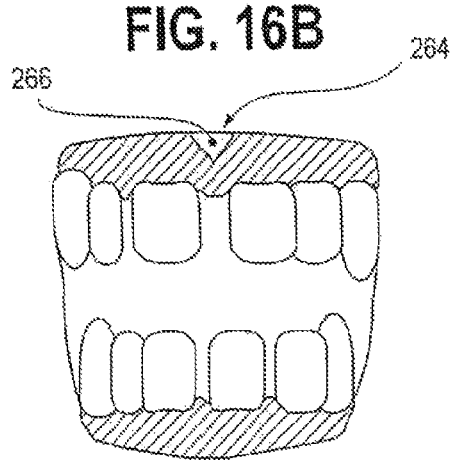
Figure 16C:
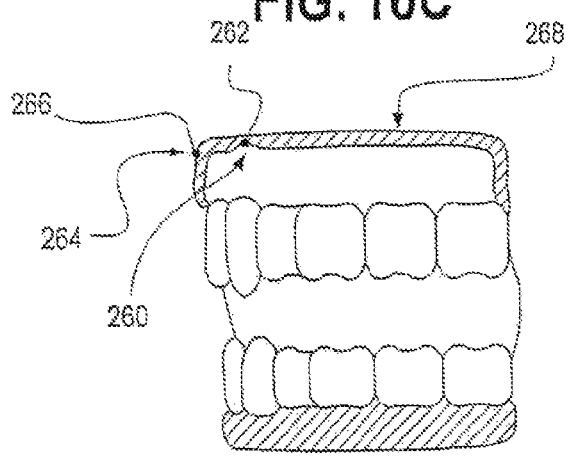

FIGS. 16A-16C illustrate a graphical diagram of selecting orientation reference points based on physical attributes of the orthodontic structure. The orientation reference points 262 and 266 will be subsequently used to map the digital image of the orthodontic structure into a three-dimensional coordinate system that will not change during the course of treatment. In this example, the frenum 264 has been selected to be one of the orientation reference points 266 and the rugae 260 has been selected as the other reference point 262. The frenum 264 is a fixed point in the orthodontic patient that will not change, or change minimally, during the course of treatment. As shown, the frenum 264 is a triangular shaped tissue in the upper-portion of the gum of the upper-arch. The rugae 260 is a cavity in the roof of the mouth 268 in the upper-arch. The rugae will also not change its physical position through treatment. As such, the frenum 264 and the rugae 260 are fixed physical points in the orthodontic patient that will not change during treatment. As such, by utilizing these as the orientation reference points 262 and 266, a three-dimensional coordinate system may be mapped thereto. Note that other physical attributes of the orthodontic patient may be used as the orientation reference points 262 and 266. However, such physical points need to remain constant throughout treatment. Accordingly, alternate physical points include the incisive papilla, cupid's bow, the inter-pupillar midpoint, inter-comissural midpoint (e.g., between the lips), inter-alar midpoint (e.g., between the sides of the nose), the prone nasale (e.g., the tip of the nose), sub-nasale (e.g., junction of the nose and the lip), a dental mid-line point, a point on the bone, a fixed bone marker such as an implant (e.g., a screw from a root canal, oral surgery).

The x, y, z coordinate system may be mapped to the physical points on the digital model of the orthodontic structure in a variety of ways. In one example, the origin of the x, y, z coordinate system may be placed at the frenum 264, the z-axis aligned with reference to the frenum and the rugae 260, and the x-axis is aligned with the midline of the upper and/or lower arch. This is further illustrated in FIGS. 17 and 18. Note that an external positioning system may be used to obtain the orientation reference points. For example, the patient may sit in a chair at a specific location of an examination room that includes a triangulation positioning system therein. As such, when the patient is scanned, the scanned images may be referenced with respect to the room's triangulation positioning system.

Figure 17:
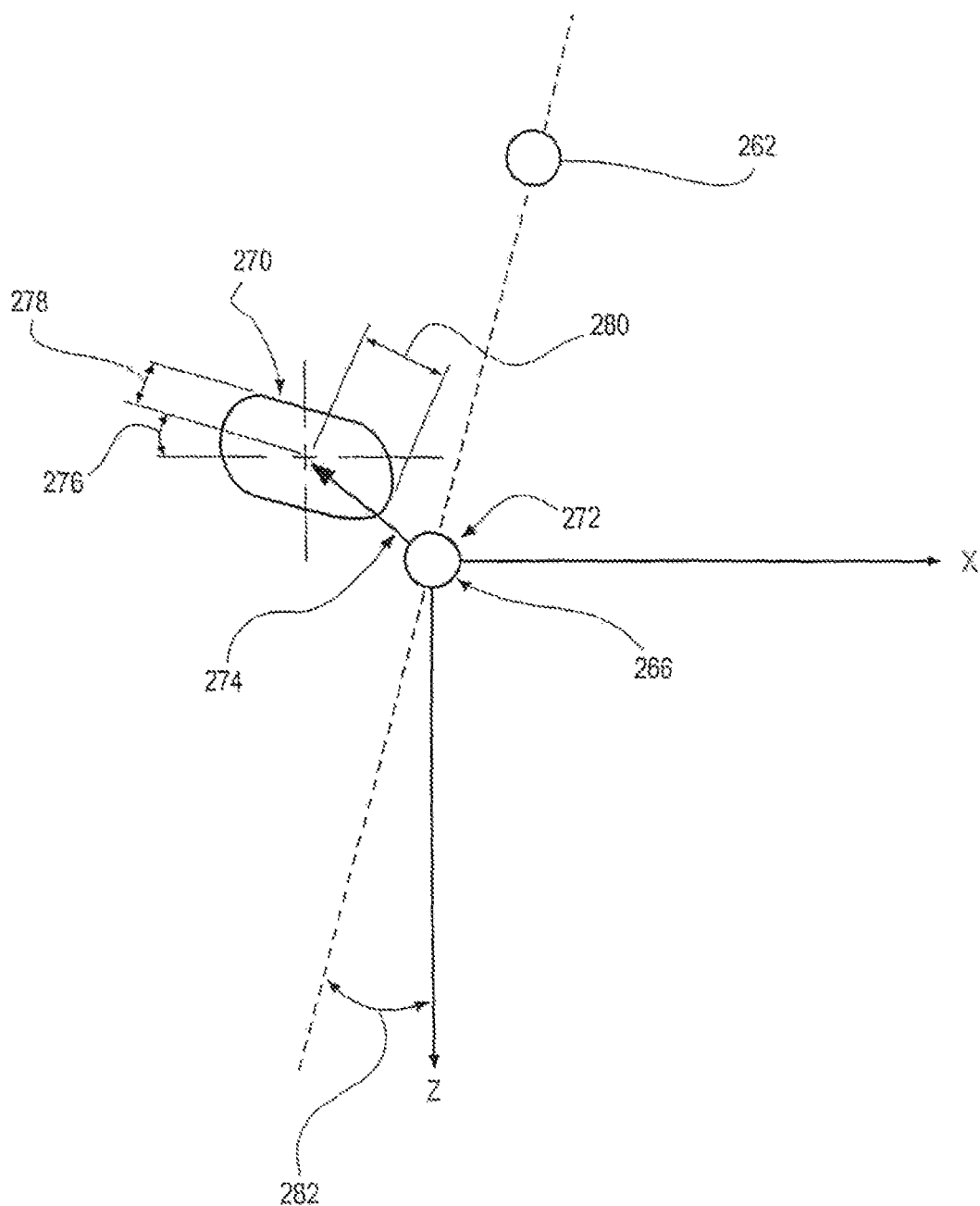
FIG. 17 is an illustration of a method of mapping the orientation reference points of FIGS. 16A-16C to a three-dimensional coordinate system.

FIG. 17 illustrates a graphical representation of mapping the orientation reference points 262 and 266 to the x-z plane of the three-dimensional x, y, z coordinate system. In this illustration, orientation point 266, which corresponds to the frenum 264, is selected as the origin of the x, y, z coordinate system. Note that any location may be selected as the origin 72. The orientation points 262 and 266 are used to determine an x, z plane orientation angle 262. Typically, the x, y, z coordinate system will be selected such that when looking at the patient from a frontal view, the x direction will be to right of the patient, the y direction towards the top of the patient's head and the z direction will be out away from the patient. As one of average skill in the art will appreciate, the orientation of the x, y, z plane may be in any orientation with respect to the reference points 262 and 266.

Figure 18:
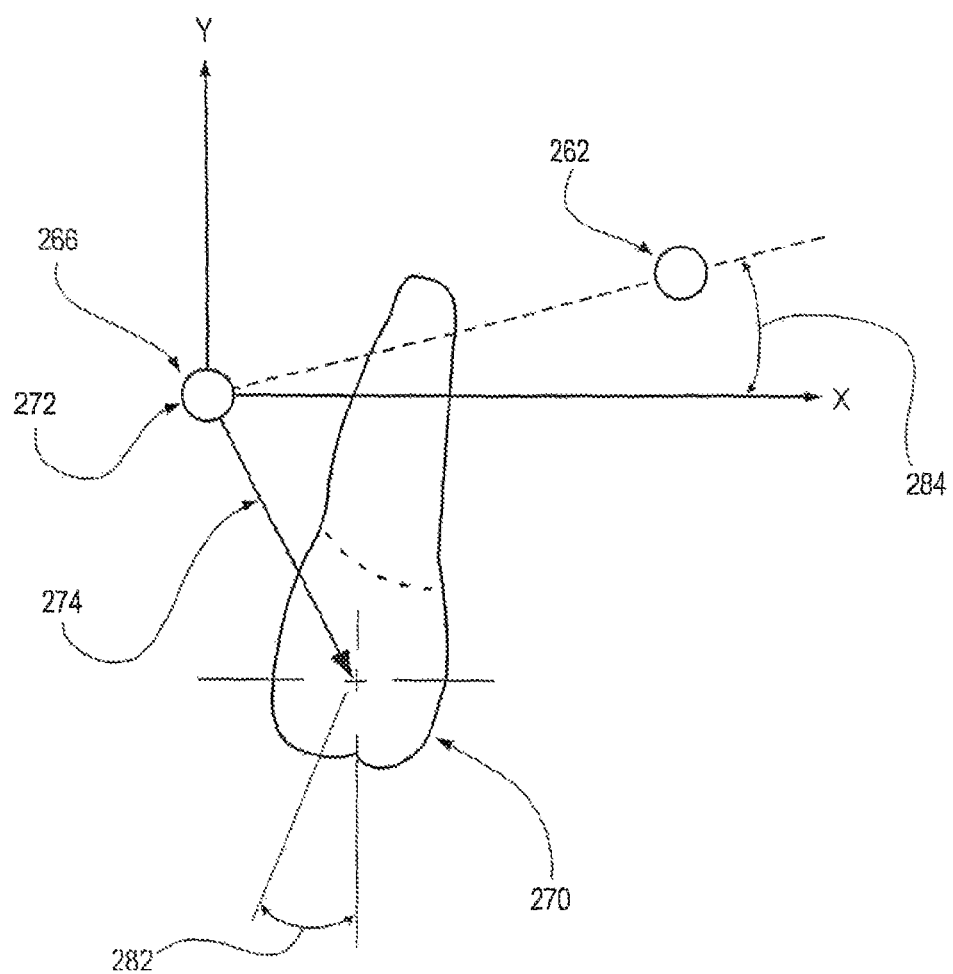
FIG. 18 is an illustration of a method of mapping the orientation reference points of FIGS. 16A-16C to a three-dimensional coordinate system.

The x-y plane is mapped to the orientation reference point 262 and 266 as shown in FIG. 18. The orientation reference point 262 and 266 are used to generate an x-y plane orientation angle 284. Based on the x-y plane orientation angle 284 and the x-z plane orientation angle 262, a digital model of a tooth 270 may be positioned in three-dimensional space with respect to the x, y, z coordinate system. As shown in FIGS. 17 and 18, the digital model of the tooth 270 includes a tooth depth 278, an angle of rotation 276 with respect to the x-z axis, an angle of rotation 282 with respect to the x-y plane, a positioning vector 274 which is in a three-dimensional space, the length of the tooth including the crown dimension, and the root dimension. Accordingly, each tooth is then mapped into the x, y, z coordinate system based on the tooth's center, or any other point of the tooth, and the dimensions of the digital model of the corresponding tooth. Once each tooth has been placed into the x, y, z coordinate system, the digital model of the tooth is complete. Note that the lower-arch is also referenced to the x, y, z coordinate system wherein the determination is made based on the occlusal plane of the patient's orthodontic structure. Alternatively, the lower-arch may include a separate three-dimensional coordinate system that is mapped to the coordinate system of the upper-arch. In this latter example, fixed points within the lower-arch would need to be determined to produce the lower arch's three-dimensional coordinate system.

Treatment Planning

The computer or workstation 10 (FIG. 1) that includes the software for generating the patient model preferably includes interactive treatment planning software that allows the user to simulate various possible treatments for the patient on the workstation and visualize the results of proposed treatments on the user interface by seeing their effect on the visual appearance of the patient, especially their smile. The interactive treatment planning preferably provides suitable tools and icons that allow the user to vary parameters affecting the patient. Such parameters would include parameters that can be changed so as to simulate change in the age of the patient, and parameters that allow the user to adjust the color, texture, position and orientation of the teeth, individually and as a group. The user manipulates the tools for these parameters and thereby generates various virtual patient models with different features and smiles. The patient models are displayed on the user interface of the workstation where they can be shared with the patient directly. Alternatively, the workstation can be coupled to a color printer. The user would simply print out hard copies of the screen shots showing the virtual patient model. Additional features related to treatment planning are disclosed in the patent application of Rohit Sachdeva filed concurrently, entitled METHOD AND SYSTEM FOR INTEGRATED ORTHODONTIC TREATMENT PLANNING USING UNIFIED WORKSTATION, Ser. No. 10/428,461.

The manner in which the software is written to provide tools allowing for simulation of various parameters can vary widely and is not considered especially critical. One possibility is a Windows-based system in which a series of icons are displayed, each icon associated with a parameter. The user clicks on the icon, and a set of windows are displayed allowing the user to enter new information directing a change in some aspect of the model. The tools could also include slide bars, or other features that are displayed to the user and tied to specific features of the patient's anatomy. Treatment planning icons for moving teeth are disclosed in the published PCT application of OraMetrix, Inc., publication no. WO 01/80761 and cited previously, which gives some idea of the types of icons and graphical user interface tools that could be used directly or adapted to simulate various parameters. Other possibilities are disclosed in the patent application of Rohit Sachdeva filed concurrently, entitled METHOD AND SYSTEM FOR INTEGRATED ORTHODONTIC TREATMENT PLANNING USING UNIFIED WORKSTATION, Ser. No. 10/428,461.

Once the user has modified the virtual patient model to achieve the patient's desired feature and smile, it is possible to automatically back-solve for the teeth, jaw and skull movement or correction necessary to achieve this result. In particular, the tooth movement necessary can be determined by isolating the teeth in the virtual patient model, treating this tooth finish position as the final position in the interactive treatment planning described in the published OraMetrix PCT application, designing the bracket placement and virtual arch wire necessary to move teeth to that position, and then fabricating the wire and bracket placement trays, templates or jigs to correctly place the brackets at the desired location. The desired jaw movement can be determined by comparing the jaw position in the virtual patient model's finish position with the jaw position in the virtual patient model in the original condition, and using various implant devices or surgical techniques to change the shape or position of the jaw to achieve the desired position.

The virtual patient model as described herein provides a common set of data that is useable in a variety of orthodontic or other treatment regimes. For example, the initial and final (target) digital data sets of the patient's tooth positions can be relayed to a manufacturer of customized transparent removable aligning shells for manufacture of a series of aligning devices, as taught in the Chisti et al. patents cited previously. Alternatively, the tooth positions may be used to derive customized bracket prescriptions for use with a flat planar archwire or other non-planar archwire. Furthermore, surgical devices such as surgical archwires, splints, prosthetic devices, and restorative devices can be fabricated with these data sets. Methods of fabricated customized archwires from data sets indicating bracket position and tooth geometry are disclosed in the patent application of Werner Butscher et al., Ser. No. 09/834,967. allowed, which is incorporated by reference herein. Methods of fabricating bracket placement jigs are described in U.S. patent application Ser. No. 09/560,127, allowed, the contents of which are incorporated by reference herein.

The choice of which treatment modality, and whether to use any additional treatment or therapeutic approaches (including surgery) will depend on the patient in consultation with the treating physician. The integrated environment proposed herein provides essentially a platform for a variety of possible treatment regimes. Further, the creation and display of the virtual patient model provides for new opportunities in patient diagnosis and sharing of patient information across multiple specialties in real time over communications networks.

Figure 19:
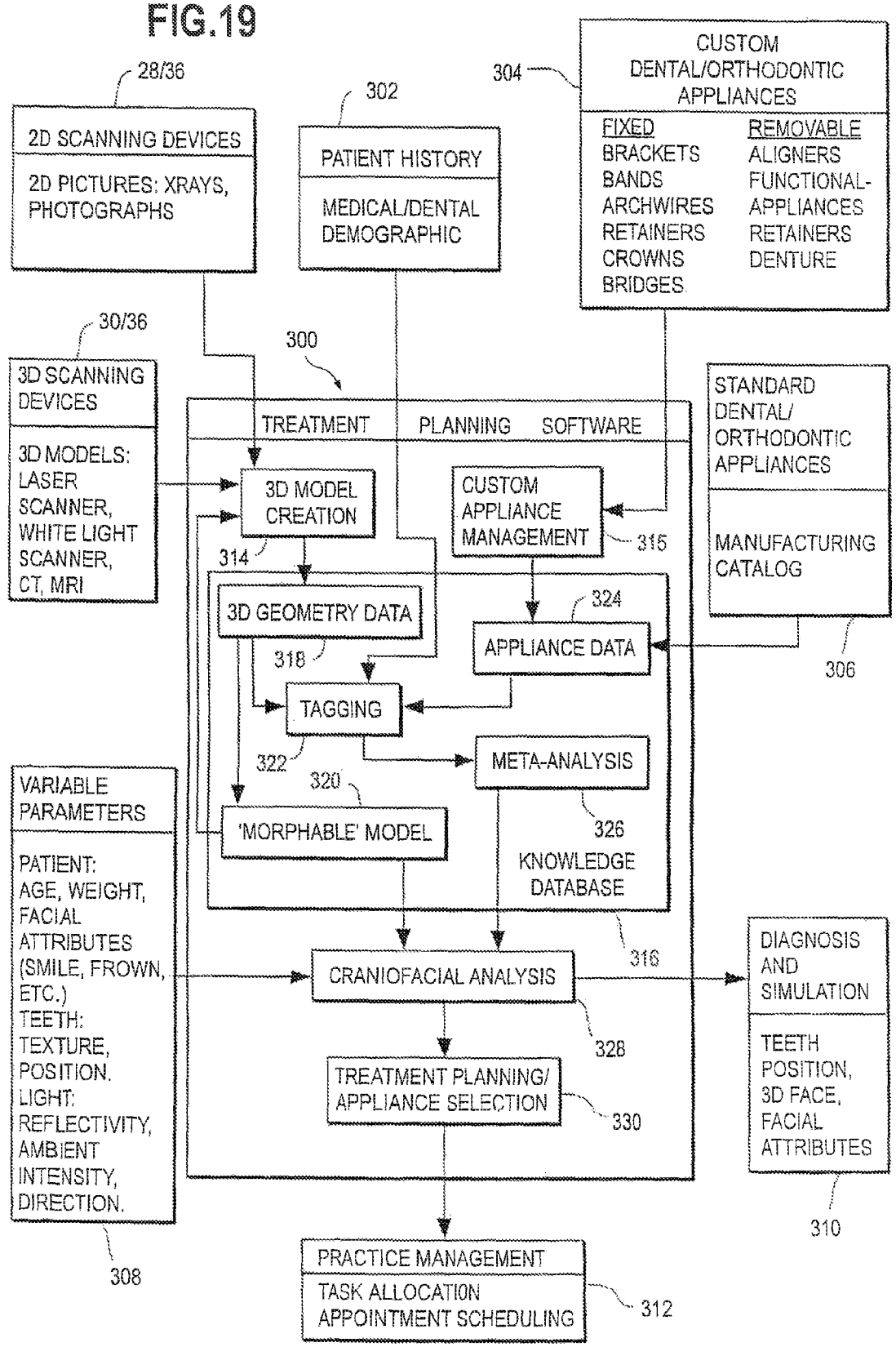
FIG. 19 is a more detailed block diagram of treatment planning software executed by the workstation of FIG. 1.

FIG. 19 is a block diagram of an integrated workstation environment for creation of the virtual patient model and diagnosis, treatment planning and delivery of therapeutics. The workstation environment shown in block diagram form in FIG. 19 may incorporate many of the hardware aspects shown in FIG. 1, including scanning or imaging devices 28/36 for capturing two dimensional images, such as a color digital camera or X-Ray machine. The workstation environment will preferably include scanning or imaging devices 30/36 for capturing three dimensional images and creating 3D models of the patient, including one or more of the following: laser scanners for scanning a plaster model of the teeth, optical scanner such as the OraMetrix hand-held scanner 30 referenced in FIG. 1, CT scanner or MRI. In some instances, the scanning devices may be located at other facilities, in which case the 3D scans are obtained at another location and the 3D data is supplied to the workstation 10 (FIG. 1) over a suitable communications channel (Internet) or via a disk sent in the mail.

The workstation includes a memory storing machine readable instructions comprising an integrated treatment planning and model manipulation software program indicated generally at 300. The treatment planning instructions 300 will be described in further detail below. The treatment planning software uses additional software modules. A patient history module 302 contains user interface screens and appropriate prompts to obtain and record a complete patient medical and dental history, along with pertinent demographic data for the patient.

A module 304 contains instructions for designing custom dental and orthodontic appliances. These appliances include both fixed appliances, e.g., brackets, bands, archwires, crowns and bridges, as well as removable appliances including aligning shells, retainers and partial or full dentures. In one possible embodiment, the module 304 may be located and executed at the site of a vendor of custom orthodontic applicants. The vendor would receive an order for a custom appliance specifically to fit an individual patient. Module 34 would process this order and containing instruction for designing the appliance to fit the individual morphology and condition of the patient. The vendor would take the appliance design, manufacture the appliance in accordance with the design, and then ship the custom appliance to the practitioner. Examples of how the appliance design module 304 might be implemented include the appliance design software developed by OraMetrix and described in the published PCT patent application cited previously, the customized bracket, jig and wire appliance design software of Ormco described in the issued Andreiko patents (see, e.g., U.S. Pat. No. 5,431,562) and in the published patent application of Chapoulaud, US patent publication no. 2002/002841, the techniques of Chisti et al., U.S. Pat. Nos. 6,227,850 and 6,217,325, all incorporated by reference herein.

The treatment planning software 300 also obtains information on standard ("off the shelf") dental or appliances from a module 306, which stores manufacturer catalogs of such appliances, including 3D virtual models of the individual appliances.

The treatment planning software includes a module 308 that allows the user to input selections as to variable parameters that affect the visual appearance of the patient, as input to a craniofacial analysis module 328 described below. The variable parameters include patient factors: age, weight, sex, facial attributes (smile, frown, etc.). The variable parameters also include parameters affecting the teeth, including texture (color), position, spacing, occlusion, etc. The variable parameters further include various illumination parameters, including reflectivity of the skin, ambient light intensity, and light direction. These parameters are accessed though appropriate icons on the screen display, such as the icons shown in FIGS. 4-7, and pop-up displays that appear that prompt the user to enter or vary the selected variable parameter.

The treatment planning software further uses a diagnosis and simulation module 310 that displays diagnosis data graphically and/or in report format. This diagnosis data includes teeth position, 3D face and smile appearance, and various facial attributes.

The software further includes third party practice management software 312. Information about treatment plans generated by the craniofacial analysis module 328 is input to the practice management software 312. Based on the treatment plan, this software generates the most productive scheduling of appointments for the patient. The practice management software 312 also generates reports, provides insurance and benefit tracking, and supports electronic claims filing with the patient's insurance company. Preferably, the practice management software provides a flexible scheduling of patient appointments based on progress of treatment of the patient's craniofacial anatomical structures. The progress of treatment is obtained from periodically obtaining updated three-dimensional information regarding the progress of treatment of the craniofacial features of the patient. For example, the patient is periodically rescanned during the course of treatment. A new virtual patient model is created. Depending on the progress of treatment (e.g., movement of the teeth to target positions) the patient may be scheduled for more or less frequent visits depending on their progress.

Referring again generally to the treatment planning software 300, the software includes a 3D model generation module 314 that uses as input the 2D and 3D scanning devices. A 3D virtual model of the patient is created by module 314, for example, in the manner described previously in FIGS. 2 and 3.

The system further includes a custom appliance management module 315. This module provides appliance specifications and 3D geometry data to the vendor site for the purpose of providing necessary input for the design and manufacture of custom appliances, such as custom orthodontic appliances, for the patient. This module also provides updates to an appliance data module 324 for storing custom appliance data within the database. The module 324 is responsible for managing the database of all the appliances, including custom appliances.

The 3D virtual patient model is supplied to a knowledge database 316. The knowledge database includes a 3D Geometry data file 316 that stores the 3D geometry data of the virtual patient model. This data is supplied to a tagging module 322 and a morphable model module 320. The morphable model module 320 includes instructions for creating a morphable model from various 3D model samples, using the techniques for example set forth in the article of Blantz et al., *A Morphable Model for The Synthesis of 3D Faces*, Computer Graphics Proceedings SIGGRAPH '99 (August, 1999).

The tagging module 322 includes instructions for tagging or placing pieces of information regarding the virtual patient model into each patient record, which is used for statistical procedures. In particular, the tagged information is supplied to a meta-analysis module 326. The meta-analysis module implements a set of statistical procedures designed to accumulate experimental and correlational results across independent studies that address a related set of research questions. Meta-analysis uses the summary statistics from individual studies as the data points. A key assumption of this analysis is that each study provides a different estimate of the underlying relationship. By accumulating results across studies, one can gain a more accurate representation of the relation than is provided by the individual study estimators. In one example, the software will use previous patient cases/studies to help in the craniofacial analysis module 328. For example, surgery cases for "lip and chin" will be one set of independent studies, whereas jaw surgery to correctly position the upper and lower jaw will be another. Another example is pathology exhibited by the patient to drive the treatment plan through meta-analysis. An orthodontist trying to align the upper and lower jaw will do a meta-analysis with the module 326 in order to see how this treatment will affect the patient's lip and chin.

The output of the morphable model from module 320 and the meta-analysis from module 326 is provided to a craniofacial analysis module 328. This module takes as input, patient information and the patient 3D virtual model to generate diagnosis and simulation data. Based on one or more simulation results, this module 328, and/or module 330 generates a treatment plan and appliance selection. User involvement is contemplated in modules 328 and 330. In particular, the user may interact with the patient information and the morphable model, and vary the parameters 308, to simulate different possible treatments and outcomes to arrive at a final or target treatment objective for the patient. The craniofacial analysis module 328 may include some or all of the treatment planning features described at length in the published PCT application of OraMetrix, Inc. cited previously.

The software instructions included in the craniofacial analysis module 326 preferably includes a set of instructions providing the user with user interface tools (e.g., icons), for visually studying on the user interface 16 the interaction of the craniofacial anatomical structures and their relationship to the external, visual appearance of the patient. For example, tools may provide a chewing simulation. Alternatively, the tools may provide a smile function in which the face is morphed to smile, showing the position of the teeth, gums, lips and other structures. These tools simulate changes in the anatomical position or shape of craniofacial anatomical structures (teeth, lips, skin, etc.) and show the effect of such changes on the visual appearance of the patient. As another example, the tools may include tools for modifying the shape or position of one or more bones of the upper and lower jaws, and show how those modifications affect the patient's appearance and smile.

With reference to FIG. 7, the user would activate one of the icons 35 at the top of the screen display. The icon may be associated with a function that would allow the user to reposition the location of the upper and lower teeth. After the user changes the position of the teeth, the user would activate another icon, "smile", and the face would morph to a smile with the teeth in the new position.

After the patient simulations have been completed and the patient and physician are satisfied, the resulting data set of teeth position, jaw position, etc. are stored by the diagnosis and simulation module 310 of FIG. 19. This module 310 preferably includes a routine for storing a three-dimensional representation of said patient's craniofacial structures (e.g., teeth) in a format suitable for use by a manufacturer of orthodontic appliances. Each manufacturer may have a unique format needed for use by the manufacturer, and the routine takes that into consideration in storing the data. For example, a manufacturer may require 3D digital models of the teeth in initial and final positions in the form of triangle surfaces, along with archwire and bracket prescription data.

It is contemplated that the creation and usage of the virtual model may occur at the patient care site. In particular, the treating practitioner will access the scan and photographic data, create the virtual model therefrom, and perform the treatment planning and simulation described herein in their own office. Once the treatment plan is arrived at, the treating physician can export the virtual patient model or some subset of data to appliance manufacturers or specialists, as indicated in FIG. 1.

Alternatively, the virtual patient model may be created at a remote location. In this latter example, a third party, such as an appliance manufacturer, may be the entity that creates the virtual patient model and makes it available to the treating physician. In this example, the treating physician will have access to the scanners, X-Ray, digital camera, or other imaging device, obtain the required data from the patient, and forward such data to the third party. The third party executes the instructions to create, visualize and manipulate the virtual patient model. This model can be transmitted to the treating physician for their review and usage. Then, either the third party could create a proposed treatment for review and approval by the treating physician, or the treating physician could create the treatment plan. The plan is then transmitted to one or more appliance manufacturers for fabrication of therapeutic devices (e.g., brackets and wires, aligning shells, maxillary expansion devices, etc.)

A treatment plan created from the virtual patient model described herein may be one in which only one type of appliances, e.g. fixed of removable, is used during the entire course of the treatment. For example, the treatment plan may be one in which brackets and wires are the type of appliance that is used. Or, alternatively, the treatment plan may be one in which removable aligning shells are the type of appliance that is used.

On the other hand, the treatment plan might be such that it is a hybrid plan requiring the use of different types of appliances during the course of the treatment. In the hybrid orthodontic treatment plan, a variety of scenarios are possible. In one type of hybrid treatment plan, different types of appliances might be used at different times during the course of the treatment. For example, patient may start out with brackets and wires and shift at some point during treatment to an approach based on removable aligning shells. In another type of hybrid treatment plan, different types of appliances might be used simultaneously, for example in different portions of the mouth, for example brackets and wires could be used for certain teeth and transparent aligning shells uses for a different set of teeth. A hybrid treatment plan may be chosen right from the beginning, or it may be introduced dynamically at any stage during the treatment course.

To develop a hybrid treatment plan, the treatment planning software will preferably include features of the appliance design and treatment planning software of the manufacturers of the appliances that are used in the hybrid treatment. As one example, the treatment planning software may include the wire and bracket features of the OraMetrix treatment planning software described in the published application WO 01/80761, as well as the treatment planning software described in the Align Technologies patents to Chisti et al., U.S. Pat. Nos. 5,975,893 and 6,227,850.

The software would thus allow the user to simulate treatment with brackets and wires for part of the tooth movement to reach a particular milestone, and also design the configuration of intermediate tooth positions and configuration of removable aligning shells for the remainder of tooth movement. Alternatively, the shape of the aligning shells could be determined automatically via the treatment planning software from the tooth configuration at which the shells are first introduced to the patient and the final tooth position in accordance with the teachings of the Chisti et al. patents.

Figure 20:
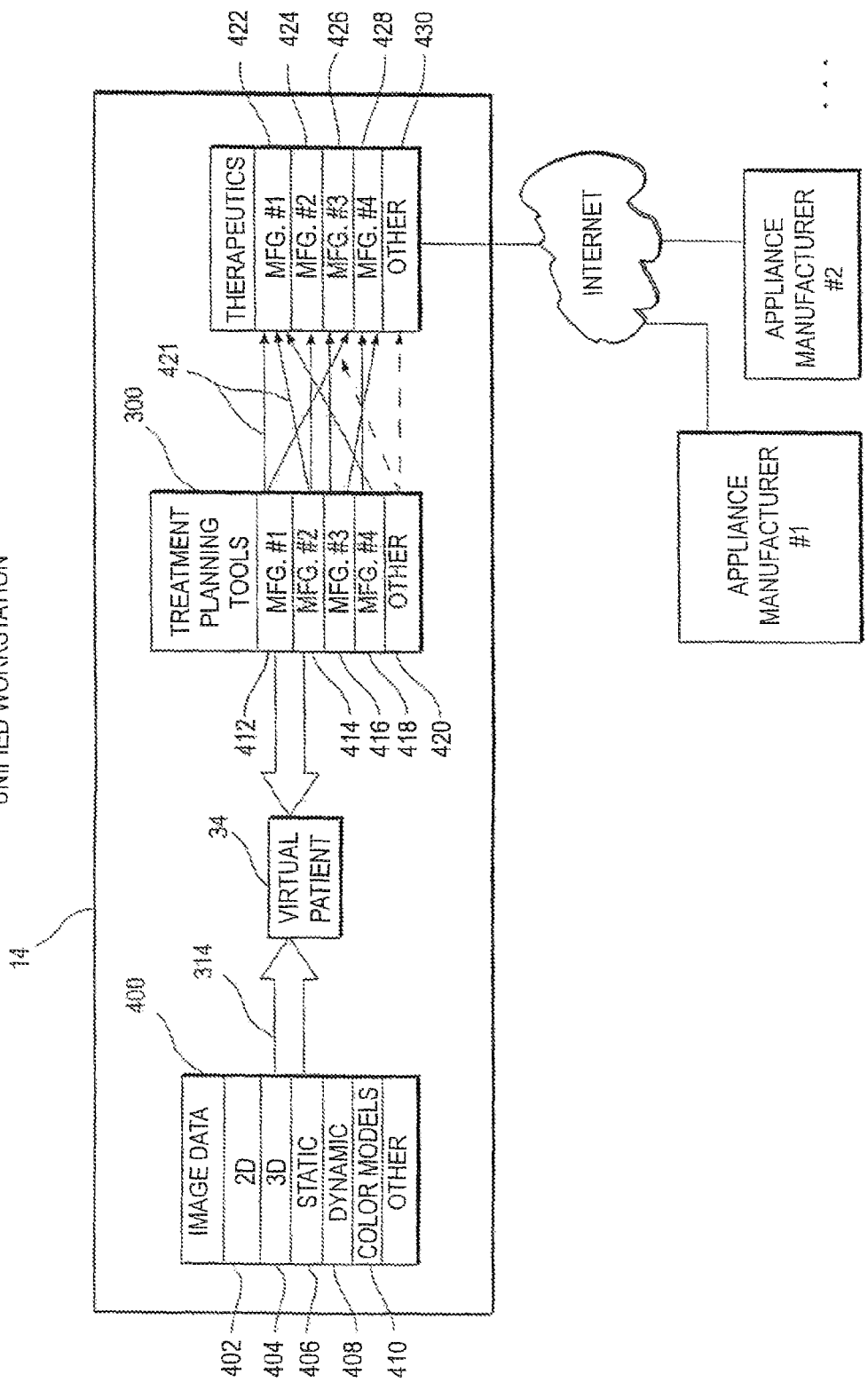
FIG. 20 is an illustration of the integration of the patient data acquisition, treatment planning and appliance design functions that are facilitated by a preferred embodiment of the unified workstation.

FIG. 20 is an illustration of the integration of the patient data acquisition, treatment planning and appliance design functions that are facilitated by a preferred embodiment of the unified workstation 14. The workstation is provided with a plurality of image data sets 400, which can include 2D data (e.g., photographs) 402, 3D image data 404 from various 3D image sources, static models 406 of all or part of the patient's craniofacial anatomy, dynamic models 408 of all or part of the patient's craniofacial anatomy, color models 410, and possibly other types of image data. The workstation 14 includes software 314 (such as described above in conjunction with FIG. 19) that takes any possible combination of this image data to produce a virtual patient model 34. From this virtual patient model, the workstation in one possible embodiment includes one or more treatment planning tools or software 300 for planning treatment for the patient. These treatment planning tools could include specific software provided by vendors of treatment planning software or appliances, such manufacturer #1 software 412, manufacturer #2 software 414, software for manufacturers nos. 3, 4, 5, 6, at 416, 418, 420, as shown. Such software would be operable on the virtual patient model 34 as described at length herein. To provide interoperability of the software on the virtual patient model, the virtual patient model may have to have representations of the data that is compatible with the software of various vendors, which is within the ability of persons skilled in this art. Moreover, once appliance designs have been created by the various species of treatment planning software, the preferred embodiment of the workstation allows export of appliance design, tooth position data or other required outputs to any appliance manufacturer so as to allow the manufacture of a customized orthodontic appliance. In other words, if the workstation is equipped with OraMetrix treatment planning software, such software could output tooth position data, appliance design data and any other required data into a format compatible with the manufacturing requirements of any appliance manufacture. This interoperability of data formats for appliance design is shown by arrows 421. Thus, the workstation provides a conversion or formatting of appliance design data into a data set or output format specified by any one of a variety of particular appliance manufacturers. In the illustrated embodiment, the available therapeutics data sets are shown as manufacturer no. 1 data set 422 (brackets and customized wires), manufacturer no. 2 data set 426 (brackets and wires), manufacturer no. 3 data set 426 (removable aligning shells), manufacturer no. 4 data set 428 (brackets and wires), or still other sets 430. The appliance design data set is then furnished over the Internet to the vendor of such appliances for manufacture of a custom appliance. Hybrid treatment plans, as described above, are one possibility of a treatment plan that may be developed using the workstation and virtual patient model described herein.

Figure 21:
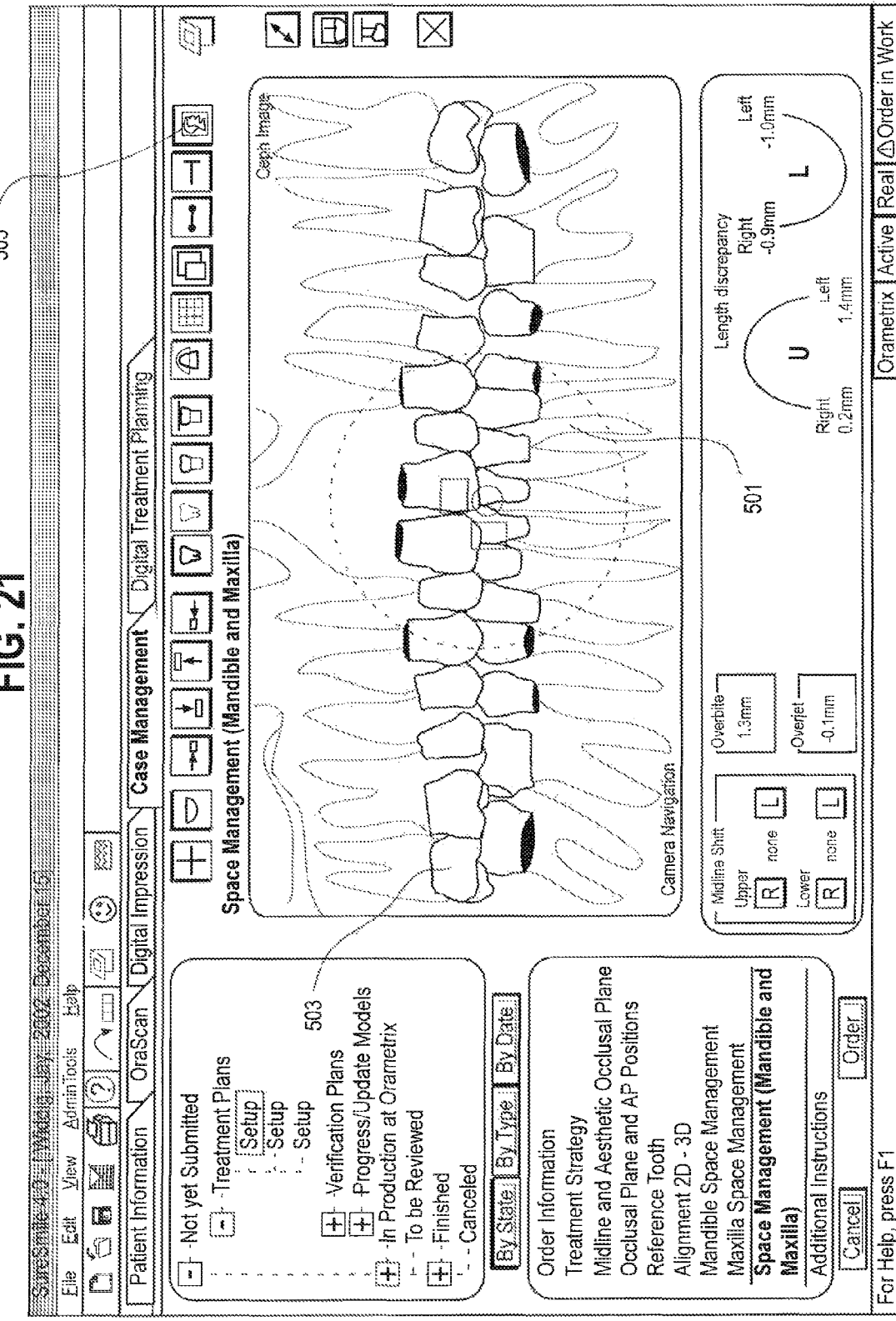
FIG. 21 is an illustration of screen display from the unified workstation showing a 3D model of teeth in a proposed tooth position for the patient; the 3D model that is flattened into a two-dimensional representation and placed in approximate registration with a two-dimensional panorama X-ray photograph, thereby assisting the user in obtaining a better understanding between the tooth roots in the current situation and the proposed tooth position in a final or ideal situation.
Figure 22:
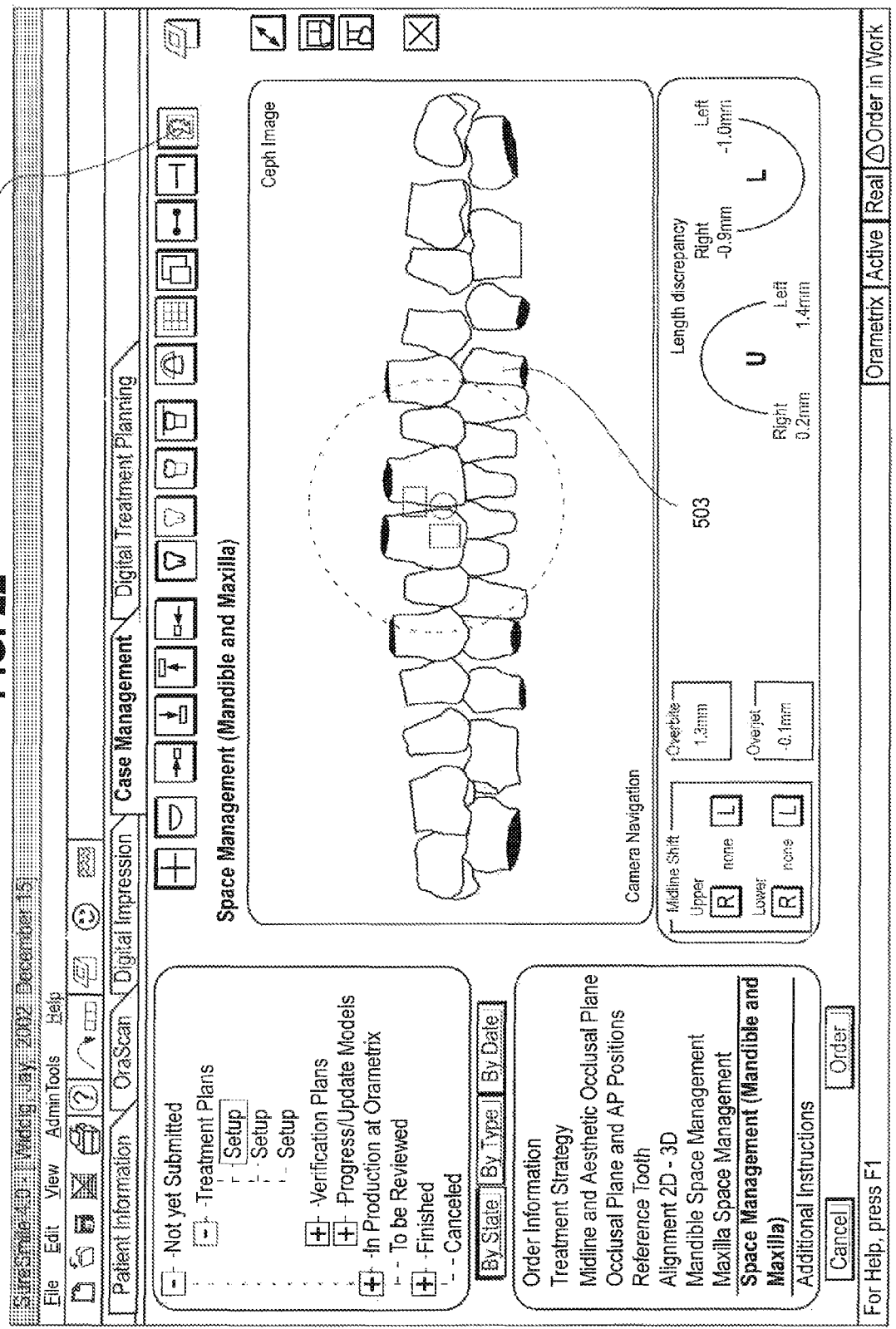
FIG. 22 is a view of the screen display similar to FIG. 21, but with the X-ray hidden so as to only show the teeth in the proposed position.

In FIGS. 21 and 22, the user has activated the icons across the top of a display on the workstation to simultaneously display both a two dimensional panoramic X-ray 501 of the teeth and jaw as well as the 3D model 503 of the teeth, but with the teeth models spread out or flattened and represented in two dimensions, in approximate registry with the panorama X-ray. The teeth models 503 that are shown in FIG. 21 represent the tooth positions in a proposed treatment. This view allows the user to judge the position of the crowns of the teeth in the proposed position relative to the position of the roots in the bone, and thereby better ascertain whether the proposed treatment is appropriate In FIG. 22, the user has unchecked the X-ray icon 505 and thus only the 3D teeth are displayed. The superposition of 3D teeth, on a 2D image of the tooth and tooth roots, as shown in FIG. 21, could be done with various different X-ray views, including biplane, lateral, lateral oblique, panorama, etc., or even 3D images which show tooth roots and associated bone structure, including CT scan images. The superposition of the 3D crowns over the tooth roots, in two or three dimensions, gives the user a new and improved tool for assessing the condition of the patient and planning treatment.

In one possible variant of the invention, the treatment planning software tools 300 are also provided at a remote location and some of the tasks of appliance design may be performed as a service by a separate workstation, such as a workstation of an appliance manufacturer. In this situation, the virtual patient model 34 could be provided to the appliance manufacturer, a proposed treatment plan is prepared and furnished to the practitioner, and after the plan is approved, the appliance manufacturer coordinates the furnishing of appliance design data to any designated appliance manufacturers that are used to furnish the custom appliance.

In one possible embodiment, the treatment planning software 300 includes a set of instructions that perform a measurement function to measure distances in two or three dimensions in the virtual patient model, e.g., arch form shape measurements, and compare the measurements with reference dimensions for an "average" patient of similar age, sex, and race. These average or "normal" measurements could be obtained in any convenient manner, for example from textbooks, organizations, practitioners, etc. These measurement tools would be invoked during the course of treatment to compare tooth movement and current tooth position with expected positions and if deviations occur, the variances could be used as information to modify one or more aspects of the treatment plan, such as change the appliance design.

Presently preferred and alternative embodiments of the invention have been set forth. Variation from the preferred and alternative embodiments may be made without departure from the scope and spirit of this invention. Furthermore, the reference in the claims to an optical scanner for scanning the dentition of the patient is intended to encompass both an in-vivo scanner scanning the teeth of the patient directly or the use of an optical, laser, destructive, or other type of scanner scanning a physical model of the teeth of the patient or an impression thereof.

Furthermore, many of the simulations involving the virtual patient model described herein that can be performed on the workstation, such as the age of the patient, the facial expression (smile, grimace, etc), the change of position of anatomical structures, etc., can be either performed as pure simulations, in which the end result is not known in advance but an intermediate change of position of a anatomical component is provided to effectuate the simulation, or as a morphing process in which the end result may be known but the intermediate steps are not known. Hence, the terms "simulation" or "simulating" in the claims are intended to encompass both pure simulations as well as morphing type operations.

We claim:

1. A method for diagnosis and planning treatment of a human patient using a computer, comprising the steps of:
    obtaining a first set of digital data representing patient craniofacial image information from a first imaging device;
    obtaining a second set of digital data representing patient craniofacial image information from a second image device different from said first image device;
    wherein said first and second sets of data representing at least in part common craniofacial anatomical structures of said patient, at least one of said first and second sets of digital data including data representing the external visual appearance or surface configuration of the face of the patient;
    wherein said first and second digital data sets are each obtained at different points in time and are not captured in a correlated fashion;
    automatically, and/or with the aid of operator interaction, superimposing said first set of digital data and said second set of digital data so as to provide a composite, combined digital representation of said craniofacial anatomical structures created from said first and second digital data sets each obtained at different points in time and not captured in a correlated fashion in a common coordinate method;
    creating a virtual 3D face at least from a portion of said craniofacial anatomical structures using an active model matching strategy; wherein said craniofacial anatomical structures include upper and lower jaws and teeth of said patient; wherein said teeth are positioned relative to each other in malocclusion position of said patient;
    displaying said composite, combined digital representation of said craniofacial anatomical structures, including said virtual 3D face, said upper and lower jaws and said teeth of said patient on a screen display of said computer using a user interface of said computer;
    making measurements of said craniofacial anatomical structures using measurement tools; and
    performing interactive treatment planning steps using said computer for planning orthodontic treatment of said patient.

2. The method of claim 1, wherein said composite, combined digital representation comprises a three-dimensional representation.

3. The method of claim 1, wherein said craniofacial anatomical structures include soft tissue of said patient.

4. The method of claim 2, wherein said craniofacial structures comprise soft tissue, bone and dentition.

5. The method of claim 2, wherein said first set of digital data comprises a set of individual tooth models representing facial components of the patient.

6. The method of claim 1, further comprising the steps of (a) visually studying on said user interface the interaction of said craniofacial anatomical structures and their relationship to the external, visual appearance of said patient; and (b) simulating changes in the anatomical position or shape of said craniofacial anatomical structures.

7. The method of claim 6, wherein said step (b) of simulating changes in the anatomical position or shape of craniofacial anatomical structures includes simulations of the effect of such changes on the external, visual appearance of said patient.

8. The method of claim 6, further comprising the steps of displaying the smile of said patient; and viewing said smile after simulation of changing the position of said craniofacial anatomical structures.

9. The method of claim 1, further comprising the steps of (a) moving said craniofacial structures; and (b) displaying the movement in a dynamic format on a user interface.

10. The method of claim 1, wherein said first set of digital data is obtained from an in-vivo scan of facial components and associated anatomical structures.

11. The method of claim 10, wherein said facial components comprise teeth.

12. The method of claim 1, wherein said first set of digital data is obtained from a scan of a model of the patients' dentition, or a scan of a facial moulage.

13. The method of claim 1, wherein said first set of data and said second set of data are obtained from imaging devices selected from the group of imaging devices consisting of digital cameras, X-ray devices, hand-held 3-D scanners, laser scanners, computed tomography (CT) scanners, MRI scanners, coordinate measuring machines, destructive scanners, and ultrasound scanners.

14. The method of claim 1, further comprising the step of storing a three-dimensional representation of said patient's craniofacial structures in a format suitable for use by a manufacturer of orthodontic appliances.

15. The method of claim 1, further comprising the step of transmitting said composite, combined digital three-dimensional representation of said craniofacial anatomical structures over a computer network.

16. The method of claim 1, wherein the orthodontic treatment comprises a hybrid treatment in which different types of appliances (fixed or removable) are selected and designed to treat the patient.

17. The method of claim 1, further comprising the step of simulating the changes in at least one of the following: the age of the patient, the facial expression of the patient, and the coloring of the skin or teeth of the patient.

18. The method of claim 1, further comprising the step of simulating the modification of the shape of any craniofacial structure.

19. The method of claim 1, further comprising the steps of merging data representing a three-dimensional scan of the surface of the face of the patient and data representing a two-dimensional color picture of the face of the patient, thereby creating a three-dimensional colored virtual model of the face of the patient.

20. The method of claim 1, wherein said first and second sets of data are obtained from imaging devices selected from the group of imaging devices consisting of two dimensional cameras, X-ray devices, hand-held 3-D scanners, laser scanners, computed tomography (CT) scanners, MRI scanners, coordinate measuring machines, destructive scanners, and ultrasound scanners; and further comprising the steps of storing a third or more sets of data representing images, including one or more X-rays of said craniofacial structures, and superimposing, either automatically or with user involvement, the three-dimensional model of said craniofacial structures from the combination of said first and second data sets with said one or more images of said craniofacial structures.

21. The method of claim 1, further comprising the step of integrating a patient management program having a scheduling feature for scheduling appointments for said patient.

22. The method of claim 21, wherein said patient management program provides a flexible scheduling of patient appointments based on progress of treatment of said craniofacial anatomical structures.

23. The method of claim 22, wherein said progress of treatment is obtained from periodically obtaining updated three-dimensional information regarding the progress of treatment of the craniofacial features of the patient.

24. The method of claim 23, wherein said three-dimensional information is obtained from scanning of the craniofacial anatomical structures with an optical, hand-held scanner.

25. The method of claim 23, wherein said craniofacial anatomical structures include the teeth of the patient.

26. The method of claim 1, further comprising the step of superimposing said first set of digital data and said second set of digital data with the use of an operator interaction, and wherein said operator interaction comprises:
displaying said first and second sets of digital data on said user interface, said operator selecting points on said user interface in said first set of data which are common to said second set of data.

27. The method of claim 1, further comprising the step of simulating changes in the position of the teeth of the patient.

28. The method of claim 1, further comprising the step of simulating changes in soft tissue of the patient.

29. The method of claim 1, wherein said composite, combined digital representation comprises a two-dimensional representation.

30. The method of claim 1, wherein said composite, combined digital representation comprises a superposition of a two-dimensional representation and a three dimensional representation.

31. The method of claim 1, further comprising the step of modeling growth in craniofacial structure of functional movement of craniofacial structures.

* * * * *